Figure 1:
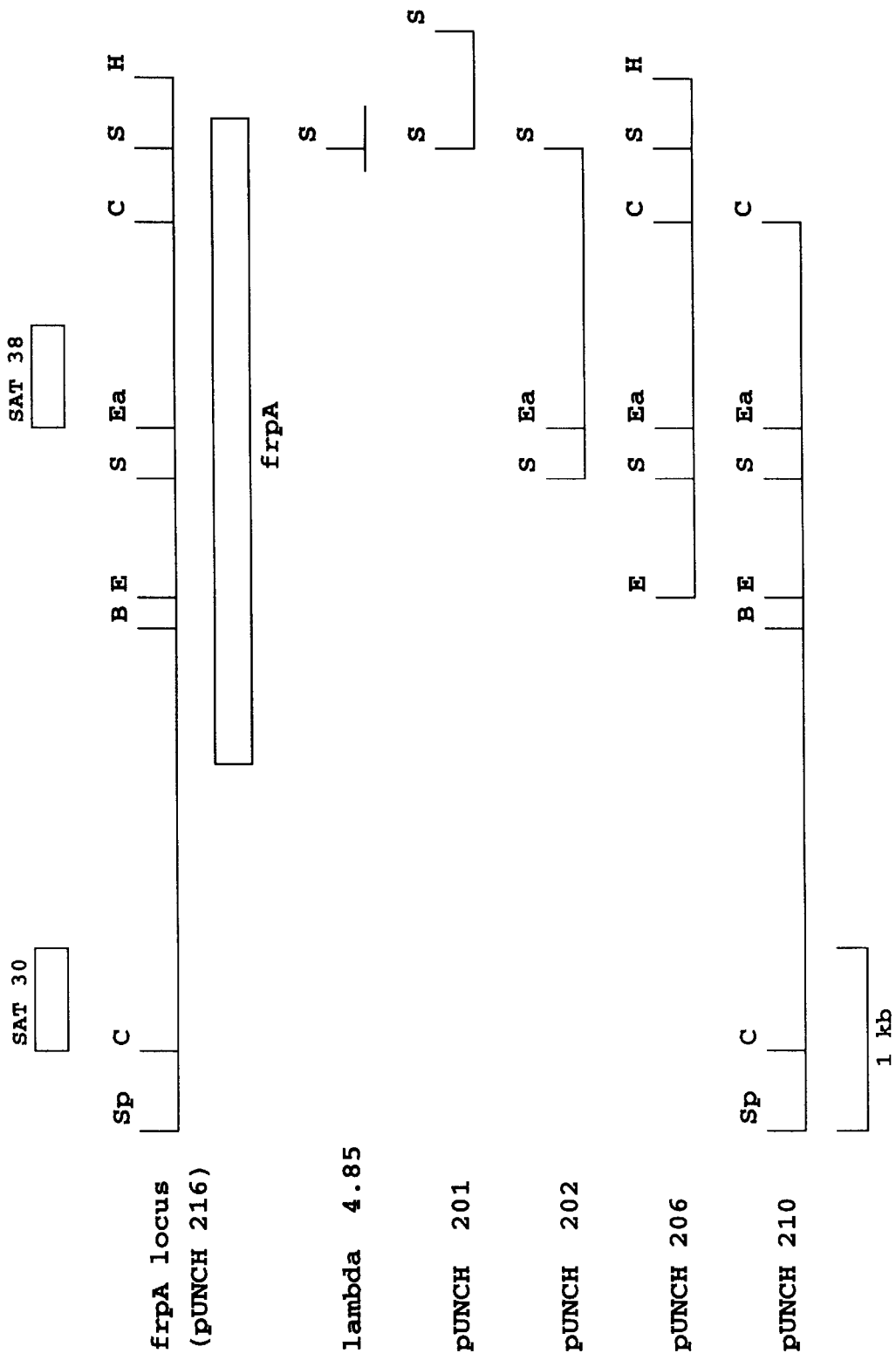

United States Patent [19]

Sparling et al.

[11] Patent Number: 6,086,896
[45] Date of Patent: Jul. 11, 2000

[54] ANTIGENIC IRON REPRESSIBLE PROTEIN FROM N. MENINGITIDIS RELATED TO THE HEMOLYSIN FAMILY OF TOXINS

[75] Inventors: P. Frederick Sparling, Moncure; Stuart Thompson, Carrboro, both of N.C.

[73] Assignee: ImClone Systems Incorporated, New York, N.Y.

[21] Appl. No.: 08/323,477

[22] Filed: Oct. 14, 1994

Related U.S. Application Data

[63] Continuation of application No. 07/920,963, Jul. 28, 1992, abandoned, which is a continuation-in-part of application No. 07/552,649, Jul. 16, 1990, abandoned.

[51] Int. Cl.[7] .................. A61K 39/095; A61K 39/02; C07K 14/22; G01N 33/53
[52] U.S. Cl. ................................... 424/250.1; 424/184.1; 424/185.1; 424/249.1; 530/350; 435/7.1
[58] Field of Search ............................... 424/250.1, 184.1, 424/185.1; 530/350; 435/69.1, 69.3, 7.1

[56] References Cited

U.S. PATENT DOCUMENTS 5,141,743   8/1992   Schryvers .................................... 424/92

FOREIGN PATENT DOCUMENTS 9203467   3/1992   WIPO .............................. C07K 3/00

OTHER PUBLICATIONS

Schryvers et al, Inf & Imm 56:1144–1149, 1988," Identification & Characterization of the Human Lactoferrin–Binding Protein from *Neisseria meningitidis*".

Conlon et al, Inf & Imm 59:587–591 1991, "Efficacy of Recombinant Leukotokin in Protection Against Pneumonic Challenge with Live Pasteurella Memolytic Al".

Thompson et al Journ. of Bact 175:811–818, 1993, "*Neisseria meningitidis* Produces Iron–regulated Proteins Related to the RTX Family of Exoproteins".

Black et al, Infect & Imm. 54:710–713 1986, Human Immune Response to Iron–Repersible Outer Membrane Protein of *Neisseria meningitidis*.

Labo et al, (Abst of Gen. Meeting of ASM, p. 31 B–37, May 1991.

Thompson et al (Abst of Gen Meeting of ASM p. 32, B–38, May 1991.

Felmlee, Dis. Abstract vol. 49, p. 1535.

Patterson, "*Neisseria meningitides* and Meningo Coccal Disease," in the Biologic and Clinical Basis of Infections Diseases, W.B. Saunders Company, Chapter 43 (1980).

Brener et al, Infection and Immunity 33, 59–66, 1981.

Welch et al, Infection and Immunity 42:178–186, 1986.

Black et al, Infection and Immunity 54:710–713, 1986.

Glaser, Molecular Biology 2:19–30, 1988.

Kolodrubetz et al, Infection and Immunity 57:1465–1469, 1989.

*Primary Examiner*—Hazel F. Sidberry
*Attorney, Agent, or Firm*—Hoffmann & Baron, LLP

[57] ABSTRACT

An isolated, antigenic polypeptide comprises a segment having at least fifty amino acid residues. The amino acid sequence of the segment is present in *N. meningitidis*, and is different from, but substantially homologous with, the amino acid sequence of a segment of a member of the hemolysin family of toxins.

3 Claims, 13 Drawing Sheets

Figure 2A

```
TATATGTCTT TATTTGAATA TATCTTACGA TGGGGAAATA TTTATATATT TTATAATAAA 060

TTTTACTCAT TTGCTAATAT GTCATGGAAT ATTACTTGTA TTTTGTAGAA TTTTTCCATA 120

TGAAAATATT CCATTTACTA TTTTTCTGAA CTTTATTAGT TTATTTTTAA TATTTTTACC 180

TCTTATATTT ACCATAAGAG AGCTAATTGA TTCATATTAT ATTGAGTCGA TAATTAATTT 240

ATTCTTAATT TTAATTCCTC ACGTTATTTT TTTAATTTAC TTGAAAGGAA AGCAGAT    297
```

| | | | | | | | | | | | | | | | | |
|---|---|---|---|---|---|---|---|---|---|---|---|---|---|---|---|---|
| ATG | ACA | TCT | GCA | AAT | TTT | AAT | ATT | AAC | GGT | TTT | GGA | GAT | GTG | AAA | TTA | 345 |
| Met | Thr | Ser | Ala | Asn | Phe | Asn | Ile | Asn | Gly | Phe | Gly | Asp | Val | Lys | Leu | |
| 1 | | | | 5 | | | | | 10 | | | | | 15 | | |
| ACA | CCC | TAT | TCA | CCA | CTC | TTG | GGA | TAT | AAA | GCT | TGG | GAT | TCA | TTT | ATT | 393 |
| Thr | Pro | Tyr | Ser | Pro | Leu | Leu | Gly | Tyr | Lys | Ala | Trp | Asp | Ser | Phe | Ile | |
| | | | 20 | | | | | 25 | | | | | 30 | | | |
| GGT | TCT | ATT | CAA | TCC | TTA | TCT | GAT | TTA | ATC | TAT | AAT | GTG | GAT | AAC | AAT | 441 |
| Gly | Ser | Ile | Gln | Ser | Leu | Ser | Asp | Leu | Ile | Tyr | Asn | Val | Asp | Asn | Asn | |
| | | 35 | | | | | 40 | | | | | 45 | | | | |
| AGA | AAT | AAA | ATG | GAA | ATT | ACT | GTT | AAT | AAT | GCT | ATC | CAA | GCT | GCA | GAT | 489 |
| Arg | Asn | Lys | Met | Glu | Ile | Thr | Val | Asn | Asn | Ala | Ile | Gln | Ala | Ala | Asp | |
| | 50 | | | | | 55 | | | | | 60 | | | | | |
| AGC | TTT | TTA | AGC | AGT | ATT | GGA | AGA | GAT | AAC | AAA | ATA | ACA | AAT | ACT | GCT | 537 |
| Ser | Phe | Leu | Ser | Ser | Ile | Gly | Arg | Asp | Asn | Lys | Ile | Thr | Asn | Thr | Ala | |
| 65 | | | | | 70 | | | | | 75 | | | | | 80 | |
| TCT | TTA | CTT | GCA | TCC | CTC | GAT | AAC | ATT | TTT | TTA | AAT | TTA | AGA | AAT | GTA | 585 |
| Ser | Leu | Leu | Ala | Ser | Leu | Asp | Asn | Ile | Phe | Leu | Asn | Leu | Arg | Asn | Val | |
| | | | | 85 | | | | | 90 | | | | | 95 | | |
| TCT | CGA | GAT | ATA | CGA | GAA | ACA | GGA | AAA | TTT | AAA | CCT | AAT | GAT | ATT | CAA | 633 |
| Ser | Arg | Asp | Ile | Arg | Glu | Thr | Gly | Lys | Phe | Lys | Pro | Asn | Asp | Ile | Gln | |
| | | | 100 | | | | | 105 | | | | | 110 | | | |
| CAA | GCA | ATT | GGT | GAT | ATA | TTC | ATT | GCT | GCT | GGT | GAT | GGA | TTA | CAA | TAT | 681 |
| Gln | Ala | Ile | Gly | Asp | Ile | Phe | Ile | Ala | Ala | Gly | Asp | Gly | Leu | Gln | Tyr | |
| | | 115 | | | | | 120 | | | | | 125 | | | | |

Figure 2B

```
ATA AAA CAA CAA ACA GAG GCG ATG GCT CAA AGC AAA TTC TTA CCA ACT    729
Ile Lys Gln Gln Thr Glu Ala Met Ala Gln Ser Lys Phe Leu Pro Thr
    130             135                 140

AAA TTA AAA ACT GGT TTA AAT GAT GTC CTT AAT TCT AGA ATG CTA AAA    777
Lys Leu Lys Thr Gly Leu Asn Asp Val Leu Asn Ser Arg Met Leu Lys
145             150                 155                 160

TCC TCT ACT GTT TTA CAG CAT GAA TTG AAT TAT TTG GGA TTT AAA ATA    825
Ser Ser Thr Val Leu Gln His Glu Leu Asn Tyr Leu Gly Phe Lys Ile
                165                 170                 175

AAG GAT TAT GGA AAC GAG AGG CTT GGC GAA TCT ATA ATG AAT ATA GAT    873
Lys Asp Tyr Gly Asn Glu Arg Leu Gly Glu Ser Ile Met Asn Ile Asp
            180                 185                 190

GAT TTT ACA CCA AGT AAG ATA GCA AAC TTT TTT GCG GAT CCT GAT ACA    921
Asp Phe Thr Pro Ser Lys Ile Ala Asn Phe Phe Ala Asp Pro Asp Thr
        195                 200                 205

TAC AGC AAT GTA TTA GAA GAA GTA TCT AGG TTT ATA TAT TCC TTA GTT    969
Tyr Ser Asn Val Leu Glu Glu Val Ser Arg Phe Ile Tyr Ser Leu Val
    210                 215                 220

CCT GAT GAT GCA AAC CCT TGG AAA GGG GGC GAA GAT TAT ATT GGA CGA   1017
Pro Asp Asp Ala Asn Pro Trp Lys Gly Gly Glu Asp Tyr Ile Gly Arg
225                 230                 235                 240

GGG ATA AGT GAA TGG GGA GAG TTA CTG GAA AAA TGG TAT AAA CAA GAT   1065
Gly Ile Ser Glu Trp Gly Glu Leu Leu Glu Lys Trp Tyr Lys Gln Asp
            245                 250                 255

TTT CTC CCT TAT CTT GAA AAA GAA TGG GAC CAA TTT CCG AAA TTT GAA   1113
Phe Leu Pro Tyr Leu Glu Lys Glu Trp Asp Gln Phe Pro Lys Phe Glu
        260                 265                 270

GAT TGG CTG CCT GAA TTC CCT GAA TGG GCA AGA GAG TGG TTG AAA TTA   1161
Asp Trp Leu Pro Glu Phe Pro Glu Trp Ala Arg Glu Trp Leu Lys Leu
    275                 280                 285

GAT CCC AAA CGT TCA GGC AAA TAT CAT GTC TAC GAC CCC CTC GCC CTA   1209
Asp Pro Lys Arg Ser Gly Lys Tyr His Val Tyr Asp Pro Leu Ala Leu
290                 295                 300
```

Figure 2C

```
GAT CTA GAC GGC GAC GGT ATA GAA ACC GTT GCT GCC AAA GGC TTT GCA    1257
Asp Leu Asp Gly Asp Gly Ile Glu Thr Val Ala Ala Lys Gly Phe Ala
305                 310                 315                 320

GGT GCA TTG TTC GAC CAC CGC AAT CAA GGC ATC CGC ACC GCC ACC GGT    1305
Gly Ala Leu Phe Asp His Arg Asn Gln Gly Ile Arg Thr Ala Thr Gly
                    325                 330                 335

TGG GTT TCT GCC GAT GAC GGT TTA CTC GTC CGC GAT TTG AAC GGC AAC    1353
Trp Val Ser Ala Asp Asp Gly Leu Leu Val Arg Asp Leu Asn Gly Asn
                340                 345                 350

GGC ATC ATC GAC AAC GGC GCG GAA CTC TTC GGC GAC AAC ACC AAA CTG    1401
Gly Ile Ile Asp Asn Gly Ala Glu Leu Phe Gly Asp Asn Thr Lys Leu
                355                 360                 365

GCA GAC GGT TCT TTT GCC AAA CAC GGC TAT GCA GCT TTG GCC GAA TTG    1449
Ala Asp Gly Ser Phe Ala Lys His Gly Tyr Ala Ala Leu Ala Glu Leu
            370                 375                 380

GAT TCA AAC GGC GAC AAC ATC ATC AAC GCG GCA GAC GCC GCA TTC CAA    1497
Asp Ser Asn Gly Asp Asn Ile Ile Asn Ala Ala Asp Ala Ala Phe Gln
385                 390                 395                 400

ACC CTG CGT GTA TGG CAG GAT CTC AAC CAG GAC GGC ATT TCC CAA GCT    1545
Thr Leu Arg Val Trp Gln Asp Leu Asn Gln Asp Gly Ile Ser Gln Ala
                    405                 410                 415

AAT GAA TTG CGT ACC CTT GAA GAA TTG GGT ATC CAA TCT TTG GAT CTC    1593
Asn Glu Leu Arg Thr Leu Glu Glu Leu Gly Ile Gln Ser Leu Asp Leu
                420                 425                 430

GCC TAT AAA GAT GTA AAT AAA AAT CTC GGT AAC GGT AAC ACT TTG GCT    1641
Ala Tyr Lys Asp Val Asn Lys Asn Leu Gly Asn Gly Asn Thr Leu Ala
                435                 440                 445

CAG CAA GGC AGC TAT ACC AAA ACA GAC GGT ACA ACC GCA AAA ATG GGG    1689
Gln Gln Gly Ser Tyr Thr Lys Thr Asp Gly Thr Thr Ala Lys Met Gly
            450                 455                 460

GAT TTA CTT TTA GCA GCC GAC AAT CTG CAC AGC CGC TTC AAA GAC AAA    1737
Asp Leu Leu Leu Ala Ala Asp Asn Leu His Ser Arg Phe Lys Asp Lys
465                 470                 475                 480
```

Figure 2D

```
GTG GAA CTC ACT GCC GAA CAG GCA AAA GCC GCC AAT CTT GCG GGC ATC   1785
Val Glu Leu Thr Ala Glu Gln Ala Lys Ala Ala Asn Leu Ala Gly Ile
            485                 490                 495

GGC CGT CTG CGC GAT TTG CGC GAA GCT GCC GCA TTG TCC GGC GAT TTG   1833
Gly Arg Leu Arg Asp Leu Arg Glu Ala Ala Ala Leu Ser Gly Asp Leu
            500                 505                 510

GCC AAT ATG CTG AAA GCT TAT TCT GCC GCC GAA ACT AAA GAA GCA CAG   1881
Ala Asn Met Leu Lys Ala Tyr Ser Ala Ala Glu Thr Lys Glu Ala Gln
            515                 520                 525

TTG GCA TTG TTA GAT AAT TTG ATT CAC AAA TGG GCG GAA ACC GAT TCG   1929
Leu Ala Leu Leu Asp Asn Leu Ile His Lys Trp Ala Glu Thr Asp Ser
            530                 535                 540

AAC TGG GGC AAA AAA TCG CCA ATG CGA CTT TCA ACC GAT TGG ACG CAA   1977
Asn Trp Gly Lys Lys Ser Pro Met Arg Leu Ser Thr Asp Trp Thr Gln
545                 550                 555                 560

ACG GCT AAT GAA GGT ATT GCA CTG ACA CCA TCC CAA GTA GCA CAA CTA   2025
Thr Ala Asn Glu Gly Ile Ala Leu Thr Pro Ser Gln Val Ala Gln Leu
            565                 570                 575

AAA AAG AAC GCT TTA GTT TCC CTT TCT GAT AAA GCT AAA GCA GCT ATT   2073
Lys Lys Asn Ala Leu Val Ser Leu Ser Asp Lys Ala Lys Ala Ala Ile
            580                 585                 590

GAC GCC GCC CGC GAC CGC ATT GCC GTG CTT GAT GCC TAC ACG GGG CAG   2121
Asp Ala Ala Arg Asp Arg Ile Ala Val Leu Asp Ala Tyr Thr Gly Gln
            595                 600                 605

GAT TCC AGC ACA CTC TAT TAC ATG AGC GAA GAA GAC GCG CTT AAT ATC   2169
Asp Ser Ser Thr Leu Tyr Tyr Met Ser Glu Glu Asp Ala Leu Asn Ile
            610                 615                 620

GTC AAA GTA ACC AAC GAT ACA TAC GAC CAT CTC GCC AAA AAC ATC TAC   2217
Val Lys Val Thr Asn Asp Thr Tyr Asp His Leu Ala Lys Asn Ile Tyr
625                 630                 635                 640

CAA AAC CTG TTG TTC CAA ACC CGT TTG CAG CCA TAT TTG AAT CAA ATC   2265
Gln Asn Leu Leu Phe Gln Thr Arg Leu Gln Pro Tyr Leu Asn Gln Ile
            645                 650                 655
```

Figure 2E

| | | | | | | | | | | | | | | | | |
|---|---|---|---|---|---|---|---|---|---|---|---|---|---|---|---|---|
| AGT | TTC | AAA | ATG | GAA | AAT | GAT | ACG | TTC | ACT | TTG | GAT | TTT | AGT | GGT | CTT | 2313 |
| Ser | Phe | Lys | Met | Glu | Asn | Asp | Thr | Phe | Thr | Leu | Asp | Phe | Ser | Gly | Leu | |
| | | | 660 | | | | | 665 | | | | | 670 | | | |
| GTT | CAA | GCA | TTT | AAC | CAT | GTC | AAA | GAA | ACT | AAT | CCG | CAA | AAA | GCT | TTT | 2361 |
| Val | Gln | Ala | Phe | Asn | His | Val | Lys | Glu | Thr | Asn | Pro | Gln | Lys | Ala | Phe | |
| | | 675 | | | | | 680 | | | | | 685 | | | | |
| GTG | GAT | TTG | GCC | GAG | ATG | CTT | GCA | TAT | GGC | GAA | CTT | CGT | TCT | TGG | TAT | 2409 |
| Val | Asp | Leu | Ala | Glu | Met | Leu | Ala | Tyr | Gly | Glu | Leu | Arg | Ser | Trp | Tyr | |
| | | 690 | | | | 695 | | | | | 700 | | | | | |
| GAA | GGC | CGA | AGA | CTA | ATG | GCC | GAT | TAT | GTG | GAG | GAG | GCA | AAA | AAA | GCA | 2457 |
| Glu | Gly | Arg | Arg | Leu | Met | Ala | Asp | Tyr | Val | Glu | Glu | Ala | Lys | Lys | Ala | |
| 705 | | | | | 710 | | | | | 715 | | | | | 720 | |
| GGT | AAA | TTT | GAA | GAT | TAC | CAG | AAA | GTG | TTG | GGT | CAG | GAG | ACC | GTT | GCA | 2505 |
| Gly | Lys | Phe | Glu | Asp | Tyr | Gln | Lys | Val | Leu | Gly | Gln | Glu | Thr | Val | Ala | |
| | | | | 725 | | | | | 730 | | | | | 735 | | |
| TTA | TTA | GCT | AAA | ACA | TCG | GGT | ACG | CAA | GCA | GAT | GAT | ATC | CTG | CAA | AAT | 2553 |
| Leu | Leu | Ala | Lys | Thr | Ser | Gly | Thr | Gln | Ala | Asp | Asp | Ile | Leu | Gln | Asn | |
| | | | 740 | | | | | 745 | | | | | 750 | | | |
| GTA | GGC | TTT | GGT | CAT | AAT | AAA | AAT | GTT | TCT | TTA | TAT | GGT | AAT | GAC | GGC | 2601 |
| Val | Gly | Phe | Gly | His | Asn | Lys | Asn | Val | Ser | Leu | Tyr | Gly | Asn | Asp | Gly | |
| | | | 755 | | | | | 760 | | | | | 765 | | | |
| AAC | GAC | ACT | CTA | ATC | GGC | GGT | GCA | GGC | AAT | GAT | TAC | TTG | GAG | GGC | GGC | 2649 |
| Asn | Asp | Thr | Leu | Ile | Gly | Gly | Ala | Gly | Asn | Asp | Tyr | Leu | Glu | Gly | Gly | |
| | | 770 | | | | | 775 | | | | | 780 | | | | |
| AGC | GGT | TCG | GAT | ACT | TAT | GTC | TTC | GGC | AAA | GGC | TTC | GGT | CAG | GAT | ACG | 2697 |
| Ser | Gly | Ser | Asp | Thr | Tyr | Val | Phe | Gly | Lys | Gly | Phe | Gly | Gln | Asp | Thr | |
| 785 | | | | | 790 | | | | | 795 | | | | | 800 | |
| GTC | TAT | AAT | TAC | GAC | TAC | GCT | ACC | GGA | CGC | AAA | GAC | ATC | ATC | CGC | TTT | 2745 |
| Val | Tyr | Asn | Tyr | Asp | Tyr | Ala | Thr | Gly | Arg | Lys | Asp | Ile | Ile | Arg | Phe | |
| | | | | 805 | | | | | 810 | | | | | 815 | | |
| ACC | GAC | GGT | ATT | ACA | GCC | GAT | ATG | CTG | ACT | TTT | ACC | CGA | GAG | GGC | AAC | 2793 |
| Thr | Asp | Gly | Ile | Thr | Ala | Asp | Met | Leu | Thr | Phe | Thr | Arg | Glu | Gly | Asn | |
| | | | 820 | | | | | 825 | | | | | 830 | | | |

Figure 2F

```
CAT CTT CTT ATC AAG GCA AAA GAC GAC AGT GGA CAA GTG ACT GTT CAG   2841
His Leu Leu Ile Lys Ala Lys Asp Asp Ser Gly Gln Val Thr Val Gln
        835             840                 845

TCC TAT TTC CAG AAC GAT GGC TCA GGT GCT TAC CGT ATC GAT GAG ATT   2889
Ser Tyr Phe Gln Asn Asp Gly Ser Gly Ala Tyr Arg Ile Asp Glu Ile
    850                 855                 860

CAT TTC GAT AAC GGC AAA GTA CTG GAT GTT GCC ACT GTC AAA GAA CTG   2937
His Phe Asp Asn Gly Lys Val Leu Asp Val Ala Thr Val Lys Glu Leu
865                 870                 875                 880

GTA CAG CAA TCC ACC GAC GGT TCG GAC AGA TTG TAT GCC TAC CAA TCC   2985
Val Gln Gln Ser Thr Asp Gly Ser Asp Arg Leu Tyr Ala Tyr Gln Ser
            885                 890                 895

GGA AGT ACC TTA AAT GGC GGA TTG GGC GAT GAC TAT CTG TAC GGT GCC   3033
Gly Ser Thr Leu Asn Gly Gly Leu Gly Asp Asp Tyr Leu Tyr Gly Ala
            900                 905                 910

GAC GGG AAT GAC CTG CTG AAT GGT GAT GCA GGC AAC GAC AGT ATC TAC   3081
Asp Gly Asn Asp Leu Leu Asn Gly Asp Ala Gly Asn Asp Ser Ile Tyr
        915                 920                 925

AGT GGC AAT GGC AAT GAT ACG CTC GAT GGA GGA GAA GGC AAC GAC GCC   3129
Ser Gly Asn Gly Asn Asp Thr Leu Asp Gly Gly Glu Gly Asn Asp Ala
    930                 935                 940

CTG TAC GGC TAT AAT GGT AAC GAT GCA CTG AAT GGT GGC GAA GGC AAT   3177
Leu Tyr Gly Tyr Asn Gly Asn Asp Ala Leu Asn Gly Gly Glu Gly Asn
945                 950                 955                 960

GAT CAT TTG AAC GGC GAA GAC GGT AAC GAC ACT CTA ATC GGC GGT GCA   3225
Asp His Leu Asn Gly Glu Asp Gly Asn Asp Thr Leu Ile Gly Gly Ala
            965                 970                 975

GGC AAT GAT TAC TTG GAG GGC GGC AGC GGT TCG GAT ACT TAT GTC TTC   3273
Gly Asn Asp Tyr Leu Glu Gly Gly Ser Gly Ser Asp Thr Tyr Val Phe
            980                 985                 990

GGC GAA GGC TTC GGT CAG GAT ACG GTC TAT AAT TAC CAT GTG GAT AAA   3321
Gly Glu Gly Phe Gly Gln Asp Thr Val Tyr Asn Tyr His Val Asp Lys
            995                 1000                1005
```

Figure 2G

```
AAC TCT GAC ACT ATG CAC TTT AAA GGA TTT AAA GCA GCA GAT GTT CAT   3369
Asn Ser Asp Thr Met His Phe Lys Gly Phe Lys Ala Ala Asp Val His
        1010            1015            1020

TTT ATC CGT TCC GGA AGT GAT TTG GTG CTT AGC GCT TCT GAA CAA GAC   3417
Phe Ile Arg Ser Gly Ser Asp Leu Val Leu Ser Ala Ser Glu Gln Asp
1025            1030            1035            1040

AAC GTA CGT ATT TCC GGA TTC TTC TAT GGT GAA AAC CAT CGT GTA GAT   3465
Asn Val Arg Ile Ser Gly Phe Phe Tyr Gly Glu Asn His Arg Val Asp
                1045            1050            1055

ACA TTT GTC TTT GAT GAT GCA GCT ATC AGT AAT CCA GAT TTT GCC AAG   3513
Thr Phe Val Phe Asp Asp Ala Ala Ile Ser Asn Pro Asp Phe Ala Lys
            1060            1065            1070

TAT ATT AAT GCT GGC AAT AAT TTG GTA CAG TCT ATG TCT GTG TTC GGT   3561
Tyr Ile Asn Ala Gly Asn Asn Leu Val Gln Ser Met Ser Val Phe Gly
            1075            1080            1085

TCT AAT ACT GCT GCG ACA GGA GGA AAT GTG GAT GCC AAT ATA CAA TCC   3609
Ser Asn Thr Ala Ala Thr Gly Gly Asn Val Asp Ala Asn Ile Gln Ser
        1090            1095            1100

GTA CAG CAG CCG TTA TTG GTA ACG CCA TCT GCA TAAGGAGCCT AATCACATTC 3662
Val Gln Gln Pro Leu Leu Val Thr Pro Ser Ala
1105            1110            1115

ATGGCTTAAA CTGAAAAACA GCAATCAAGT TTATTTTGAT TGCTGTTTTT CTTAATATTG 3722

GGATAAGGGT CGAGACCTTT GCAAAAATAG TCTGTT                           3758
```

Figure 3A

```
Met Thr Ser Ala Asn Phe Asn Ile Asn Gly Phe Gly Asp Val Lys Leu
 1           5               10                  15

Thr Pro Tyr Ser Pro Leu Leu Gly Tyr Lys Ala Trp Asp Ser Phe Ile
            20              25              30

Gly Ser Ile Gln Ser Leu Ser Asp Leu Ile Tyr Asn Val Asp Asn Asn
            35              40              45

Arg Asn Lys Met Glu Ile Thr Val Asn Asn Ala Ile Gln Ala Ala Asp
        50              55              60

Ser Phe Leu Ser Ser Ile Gly Arg Asp Asn Lys Ile Thr Asn Thr Ala
 65              70              75                  80

Ser Leu Leu Ala Ser Leu Asp Asn Ile Phe Leu Asn Leu Arg Asn Val
            85              90                  95

Ser Arg Asp Ile Arg Glu Thr Gly Lys Phe Lys Pro Asn Asp Ile Gln
            100             105             110

Gln Ala Ile Gly Asp Ile Phe Ile Ala Ala Gly Asp Gly Leu Gln Tyr
        115             120             125

Ile Lys Gln Gln Thr Glu Ala Met Ala Gln Ser Lys Phe Leu Pro Thr
    130             135             140

Lys Leu Lys Thr Gly Leu Asn Asp Val Leu Asn Ser Arg Met Leu Lys
145             150             155                 160

Ser Ser Thr Val Leu Gln His Glu Leu Asn Tyr Leu Gly Phe Lys Ile
            165             170             175

Lys Asp Tyr Gly Asn Glu Arg Leu Gly Glu Ser Ile Met Asn Ile Asp
            180             185             190

Asp Phe Thr Pro Ser Lys Ile Ala Asn Phe Phe Ala Asp Pro Asp Thr
        195             200             205

Tyr Ser Asn Val Leu Glu Glu Val Ser Arg Phe Ile Tyr Ser Leu Val
    210             215             220
```

Figure 3B

Pro Asp Asp Ala Asn Pro Trp Lys Gly Gly Glu Asp Tyr Ile Gly Arg
225            230                235                240

Gly Ile Ser Glu Trp Gly Glu Leu Leu Glu Lys Trp Tyr Lys Gln Asp
            245                250                255

Phe Leu Pro Tyr Leu Glu Lys Glu Trp Asp Gln Phe Pro Lys Phe Glu
            260                265                270

Asp Trp Leu Pro Glu Phe Pro Glu Trp Ala Arg Glu Trp Leu Lys Leu
        275                280                285

Asp Pro Lys Arg Ser Gly Lys Tyr His Val Tyr Asp Pro Leu Ala Leu
    290                295                300

Asp Leu Asp Gly Asp Gly Ile Glu Thr Val Ala Ala Lys Gly Phe Ala
305                310                315                320

Gly Ala Leu Phe Asp His Arg Asn Gln Gly Ile Arg Thr Ala Thr Gly
                325                330                335

Trp Val Ser Ala Asp Asp Gly Leu Leu Val Arg Asp Leu Asn Gly Asn
            340                345                350

Gly Ile Ile Asp Asn Gly Ala Glu Leu Phe Gly Asp Asn Thr Lys Leu
        355                360                365

Ala Asp Gly Ser Phe Ala Lys His Gly Tyr Ala Ala Leu Ala Glu Leu
    370                375                380

Asp Ser Asn Gly Asp Asn Ile Ile Asn Ala Ala Asp Ala Ala Phe Gln
385                390                395                400

Thr Leu Arg Val Trp Gln Asp Leu Asn Gln Asp Gly Ile Ser Gln Ala
            405                410                415

Asn Glu Leu Arg Thr Leu Glu Glu Leu Gly Ile Gln Ser Leu Asp Leu
        420                425                430

Ala Tyr Lys Asp Val Asn Lys Asn Leu Gly Asn Gly Asn Thr Leu Ala
    435                440                445

Figure 3C

Gln Gln Gly Ser Tyr Thr Lys Thr Asp Gly Thr Thr Ala Lys Met Gly
    450                    455                  460

Asp Leu Leu Leu Ala Ala Asp Asn Leu His Ser Arg Phe Lys Asp Lys
465                  470                475                480

Val Glu Leu Thr Ala Glu Gln Ala Lys Ala Ala Asn Leu Ala Gly Ile
                485                490              495

Gly Arg Leu Arg Asp Leu Arg Glu Ala Ala Ala Leu Ser Gly Asp Leu
            500              505              510

Ala Asn Met Leu Lys Ala Tyr Ser Ala Ala Glu Thr Lys Glu Ala Gln
        515            520              525

Leu Ala Leu Leu Asp Asn Leu Ile His Lys Trp Ala Glu Thr Asp Ser
    530                535              540

Asn Trp Gly Lys Lys Ser Pro Met Arg Leu Ser Thr Asp Trp Thr Gln
545                550              555              560

Thr Ala Asn Glu Gly Ile Ala Leu Thr Pro Ser Gln Val Ala Gln Leu
            565              570              575

Lys Lys Asn Ala Leu Val Ser Leu Ser Asp Lys Ala Lys Ala Ala Ile
        580            585              590

Asp Ala Ala Arg Asp Arg Ile Ala Val Leu Asp Ala Tyr Thr Gly Gln
    595                600              605

Asp Ser Ser Thr Leu Tyr Tyr Met Ser Glu Glu Asp Ala Leu Asn Ile
    610              615            620

Val Lys Val Thr Asn Asp Thr Tyr Asp His Leu Ala Lys Asn Ile Tyr
625                630              635            640

Gln Asn Leu Leu Phe Gln Thr Arg Leu Gln Pro Tyr Leu Asn Gln Ile
            645              650              655

Ser Phe Lys Met Glu Asn Asp Thr Phe Thr Leu Asp Phe Ser Gly Leu
        660            665              670

Figure 3D

```
Val Gln Ala Phe Asn His Val Lys Glu Thr Asn Pro Gln Lys Ala Phe
        675             680             685
Val Asp Leu Ala Glu Met Leu Ala Tyr Gly Glu Leu Arg Ser Trp Tyr
    690             695             700
Glu Gly Arg Arg Leu Met Ala Asp Tyr Val Glu Ala Lys Lys Ala
705             710             715             720
Gly Lys Phe Glu Asp Tyr Gln Lys Val Leu Gly Gln Glu Thr Val Ala
            725             730             735
Leu Leu Ala Lys Thr Ser Gly Thr Gln Ala Asp Asp Ile Leu Gln Asn
        740             745             750
Val Gly Phe Gly His Asn Lys Asn Val Ser Leu Tyr Gly Asn Asp Gly
        755             760             765
Asn Asp Thr Leu Ile Gly Gly Ala Gly Asn Asp Tyr Leu Glu Gly Gly
    770             775             780
Ser Gly Ser Asp Thr Tyr Val Phe Gly Lys Gly Phe Gly Gln Asp Thr
785             790             795             800
Val Tyr Asn Tyr Asp Tyr Ala Thr Gly Arg Lys Asp Ile Ile Arg Phe
            805             810             815
Thr Asp Gly Ile Thr Ala Asp Met Leu Thr Phe Thr Arg Glu Gly Asn
        820             825             830
His Leu Leu Ile Lys Ala Lys Asp Asp Ser Gly Gln Val Thr Val Gln
        835             840             845
Ser Tyr Phe Gln Asn Asp Gly Ser Gly Ala Tyr Arg Ile Asp Glu Ile
    850             855             860
His Phe Asp Asn Gly Lys Val Leu Asp Val Ala Thr Val Lys Glu Leu
865             870             875             880
Val Gln Gln Ser Thr Asp Gly Ser Asp Arg Leu Tyr Ala Tyr Gln Ser
            885             890             895
```

Figure 3E

Gly Ser Thr Leu Asn Gly Gly Leu Gly Asp Asp Tyr Leu Tyr Gly Ala
            900             905                 910

Asp Gly Asn Asp Leu Leu Asn Gly Asp Ala Gly Asn Asp Ser Ile Tyr
            915             920             925

Ser Gly Asn Gly Asn Asp Thr Leu Asp Gly Gly Glu Gly Asn Asp Ala
    930             935             940

Leu Tyr Gly Tyr Asn Gly Asn Asp Ala Leu Asn Gly Gly Glu Gly Asn
945             950             955             960

Asp His Leu Asn Gly Glu Asp Gly Asn Asp Thr Leu Ile Gly Gly Ala
            965             970             975

Gly Asn Asp Tyr Leu Glu Gly Gly Ser Gly Ser Asp Thr Tyr Val Phe
            980             985             990

Gly Glu Gly Phe Gly Gln Asp Thr Val Tyr Asn Tyr His Val Asp Lys
        995             1000            1005

Asn Ser Asp Thr Met His Phe Lys Gly Phe Lys Ala Ala Asp Val His
    1010            1015            1020

Phe Ile Arg Ser Gly Ser Asp Leu Val Leu Ser Ala Ser Glu Gln Asp
1025            1030            1035            1040

Asn Val Arg Ile Ser Gly Phe Phe Tyr Gly Glu Asn His Arg Val Asp
                1045            1050            1055

Thr Phe Val Phe Asp Asp Ala Ala Ile Ser Asn Pro Asp Phe Ala Lys
            1060            1065            1070

Tyr Ile Asn Ala Gly Asn Asn Leu Val Gln Ser Met Ser Val Phe Gly
            1075            1080            1085

Ser Asn Thr Ala Ala Thr Gly Gly Asn Val Asp Ala Asn Ile Gln Ser
    1090            1095            1100

Val Gln Gln Pro Leu Leu Val Thr Pro Ser Ala
1105            1110            1115

ANTIGENIC IRON REPRESSIBLE PROTEIN FROM N. MENINGITIDIS RELATED TO THE HEMOLYSIN FAMILY OF TOXINS

This application is continuation of Ser. No. 07/920,963 filed Jul. 28, 1992 abandoned, which is a continuation-in-part of Ser. No. 07/552,649 filed Jul. 16, 1990 abandoned, both of which are incorporated herein by reference.

The present invention is directed to antigenic polypeptides isolated from *Neisseria meningitidis*, antibodies raised against the polypeptides, vaccines containing the polypeptides and DNA encoding the polypeptides. The polypeptides are members of the hemolysin family of toxins, a typical member of which is alpha-hemolysin from *E. coli*.

Bacterial pathogenesis is a complicated and often poorly understood process. Many pathogenic bacteria secrete toxins that impair the metabolism and function of animal cells. Various classes of molecules constitute such toxins.

An example of a protein toxin is found in pathogenic *E. coli* strains that cause extra-intestinal infections in humans. Such infections are characterized by the lysis of mammalian erythrocytes. The hemolytic activity is due to a class of toxins known as hemolysin. The class includes alpha-hemolysin and beta-hemolysin; see Welch et al, Infection and Immunity 42, 178–186 (1983).

Another protein toxin is adenylate cyclase, which is found in *Bordetella pertussis* and *Bacillus anthracis*, and which impairs functions of professional phagocytes. These bacteria are responsible for whooping cough and anthrax, respectively.

A third class of protein toxins from pathogenic bacteria are the leukotoxins, which are found in *Actinobacillus actinomycetemcomitans*, which is the etiologic agent of localized juvenile periodontitis, and *Pasteurella haemolytica*, which kills bovine leukocytes.

Interestingly, the adenylate cyclase from *B. pertussis* and *B. anthracis* and the leukotoxins from *A. actinomycetemcomitans* and *P. haemolytica* have amino acid sequences that exhibit considerable homology with that of alpha-hemolysin from *E. Coli*; see Glaser et al, Molecular Biology 2, 19–30 (1988) and Kolodrubetz et al, Infection and Immunity 57, 1465–1469 (1989). Apparently, there is a class of toxins found in various genera of bacteria. The amino acid sequence of this family of cytotoxins is characterized by a highly repeated nine amino acid motif, LxGGxGNDx, wherein x represents any amino acid. For the purposes of this specification, this family of toxins will be referred to as the hemolysin family of toxins.

It should be understood that "hemolysin family of toxins" is a generic name familiar to those in the art, and is not meant to imply that all members are hemolytic, or, for that matter, cytotoxic, although most are. Membership in the family depends on the existence of homology in the amino acid sequence, as defined below. In addition to those mentioned above, homologous proteins have also been found in Serratia and Proteus, although it is not certain whether these members of the hemolysin family are, in fact, cytotoxic.

Little is known about the intriguing and sometimes fatal bacteria *Neisseria meningitidis*, which is responsible for spinal meningitis and septic shock. *N. meningitidis* and the diseases it causes have been reviewed by Paterson in "Neisseria meningitidis and Meningococcal Disease" in *Biologic and Clinical Basis of Infectious Diseases*, W. B. Saunders Company, Chapter 43 (1980).

The genotype of *N. meningitidis* is very similar to that of *N. gonorrhoeae*, although the phenotype is quite different. It is often important to distinguish between these Neisseria species. Immunologic speciation is often difficult due to a lack of sufficient amounts of group-specific antigens.

*N. meningitidis* exists as various serotypes, the prevalence of which varies with time and location. The serotypes include A, B, C, D, X, Y, Z, 29-E and W-135.

The three most important known antigenic and/or toxic constituents of *N. meningitidis* infections are a capsular polysaccharide, a lipopolysaccharide-endotoxin cell wall complex and a Neisseria-specific protein. The capsular polysaccharide is a major virulence factor that enables meningococci to resist phagocytosis by segmented neutrophils.

Vaccines containing meningococcal polysaccharides are used against some of the serotypes of *N. meningitidis*. For example, protection against the A, C, Y and W-135 serotypes is afforded by polysaccharide vaccines. Such vaccines are, however, inadequate for general protection against infection by *N. meningitidis*. For example, the immune response of serotypes A and C to polysaccharide vaccines is poor, especially in children under two years old, who constitute the group most susceptible to meningococcal disease. Moreover, no effective vaccine exists for serotype B, possibly because the group B capsular polysaccharide is relatively non-immunogenic.

It is apparent that much needs to be learned about the pathology of *N. meningitidis*. Possibly, additional understanding of this pathogen will lead to the discovery of useful vaccines in general for more serotypes than are currently available.

For example, it is not known why the colonization of the respiratory tract by *N. meningitidis* progresses to acute meningococcal disease and sometimes death in an occasional individual, whereas it does not do so in the great majority of others who are apparently at comparable risk. The amount of neither capsular polysaccharide nor lipopolysaccharide-endotoxin complex correlates with the seriousness of this disease. Exposure to microorganisms with antigenic constituents that cross-react with capsular polysaccharides of *N. meninaitidis* has been proposed as an explanation; see Paterson, id.

Other explanations are also possible. For example, cross-immunity to antigens other than capsular polysaccharides cannot be ruled out. It is interesting to note in this regard that there are no known protein toxins associated with *N. meningitidis*. One reason for this may be that *N. meningitidis* is often cultured in vitro under iron-rich conditions that do not exist in a human host. It is known, however, that some meningococcal proteins are iron-repressed and are not observed in vitro, although they are expressed in vivo. See Black et al., Infection and Immunity 54, 710–713 (1986) and Brener et al, ibid. 33, 59–66 (1981).

One problem addressed by the present invention is the discovery of antigenic polypeptides and DNA sequences that are capable of identifying *N. meningitidis* and distinguishing it from *N. gonorrhoeae*. Another problem addressed by the present invention is the discovery of proteins capable of producing antibodies effective against meningococcal disease.

SUMMARY OF THE INVENTION

These and other problems as will be apparent to those having ordinary skill in the art have been solved by providing an isolated, antigenic polypeptide comprising a segment having at least fifty amino acid residues, wherein the amino acid sequence of the segment is present in *N. meninaitidis*, and wherein the amino acid sequence is different from, but substantially homologous with, the amino acid sequence of a segment of a member of the hemolysin family of toxins.

Another way of defining the polypeptide is to say that it is an isolated polypeptide comprising a segment having an amino acid sequence present in *N. meningitidis* wherein the amino acid sequence consists of at least three repeats of the nine amino acid hemolysin consensus sequence, the hemolysin consensus sequence consisting of at least four of:

L at position 1;
G at position 3;
G at position 4;
G at position 6;
N at position 7;
D at position 8; and X at positions 2, 5 and 9;

wherein x, independently, represents any single amino acid residue.

The invention further includes antigenic fragments of such polypeptides, antibodies raised against such polypeptides, nucleotide sequences encoding such polypeptides, and vaccines containing such polypeptides.

BRIEF DESCRIPTION OF THE FIGURES

FIG. 1 shows the relationship to one another of the restriction fragments used to obtain the frpA gene.

FIGS. 2A–2G show the DNA and amino acid sequence of the gene for an antigenic iron repressible protein (frpA) from *N. meningitidis* related to the hemolysin family of toxins. See Seq. ID No. 1.

FIGS. 3A–3E show the putative amino acid sequence for the DNA sequence of FIGS. 2A–2G. See Seq. ID No. 2.

DETAILED DESCRIPTION OF THE INVENTION

The Polypeptide Segment

It has unexpectedly been discovered that when *N. meningitidis* is grown under iron-limiting conditions, a polypeptide comprising a segment having an amino acid sequence that is different from, but substantially homologous with, a segment of the hemolysin family of toxins is expressed. Monoclonal antibodies raised against the polypeptide found in *N. meningitidis*, such as A4.85 (see below), cross-react in Western blots with alpha-hemolysin (HlyA) produced by the hlyA gene in *E. coli* and adenylate cyclase produced in *Bordetella pertussis.*

The hemolysin family of toxins, as used herein, includes the homologous, cytotoxic or proteolytic polypeptides found in bacteria of the genera Escherichia, Serratia, Pasteurella, Proteus, Actinobacillus, and Bordetella. The family specifically includes alpha-hemolysin, leukotoxin, and adenylate cyclase.

Determinations whether two amino acid sequences are substantially homologous are, for the purpose of the present specification, based on FASTA searches in accordance with Pearson and Lipman, Proc. Natl. Acad. Sci. USA 85, 2444–2448 (1988). A substantially homologous sequence in accordance with the present invention has at least 15% identity, preferably at least 20% identity and, more preferably, at least 25% identity in amino acid sequence when determined in accordance with the method of Pearson and Lipman, which is incorporated herein by reference.

The polypeptide of the present invention need not contain a segment that is identical to other members of the hemolysin family of toxins. The identity in accordance with the FASTA method may be as high as 90% or 95%, but when isolated from *N. meningitidis* normally does not exhibit identities greater than 40% or 50%.

The size of the polypeptide is not critical, as long as it contains a segment that is substantially homologous to a segment of a member of the hemolysin family of toxins. The substantially homologous segment has at least fifty amino acid residues, preferably at least 100 amino acid residues, and more preferably at least 200 amino acid residues. In this specification, the word "polypeptide" will be considered indistinguishable from words like "protein" and "peptide."

The segment of the meningococcal polypeptide that is substantially homologous to a segment of the hemolysin family of toxins contains the same nine amino acid motif that is characteristic of all the members of the hemolysin family of toxins. The consensus sequence is LxGGxGNDx, hereinafter hemolysin consensus sequence. The amino acid represented by x may be any single amino acid.

The polypeptide of the invention may be defined in terms of the hemolysin consensus sequence as well as by the substantial homology standard described above. For this purpose, a nine amino acid sequence is considered to be a hemolysin consensus sequence if it contains at least four, preferably at least five, and more preferably all six of the specifically defined amino acid residues (i.e. L-GG-GND-) at the correct position.

Referring to FIGS. 3A–3E, which, as described below, is a polypeptide isolated from *N. meninaitidis*, the homologous segment comprises two stretches of multiple repeats of the hemolysin consensus sequence, i.e. between amino acids 763 and 789; and between amino acids 900 and 989. There are 13 complete consensus sequences in FIGS. 3A–3E. See Seq. ID No. 2.

The polypeptides of the present invention contain segments that are present in *N. meningitidis* and that comprise at least three, preferably at least five, and more preferably at least ten hemolysin consensus sequences. The polypeptides of the invention may have as many as at least 21 hemolysin consensus sequences.

The polypeptide is isolated, which means that it is essentially free of other proteins, especially of other proteins from *N. meningitidis*. Essentially free from other proteins means that it is at least 90%, preferably at least 95% and, more preferably, at least 98% free of other proteins.

Preferably, the polypeptide is essentially pure, which means that the polypeptide is free not only of other polypeptides, but also of other materials used in the isolation and identification of the polypeptide, such as, for example, sodium dodecyl sulfate and other detergents as well as nitrocellulose paper. The polypeptide is at least 90% free, preferably at least 95% free and, more preferably, at least 98% free of such materials.

The polypeptide of the present invention is antigenic, which means that the polypeptide induces specific antibodies in a mammal. Preferably, the polypeptide is immunogenic.

The polypeptide may be the entire polypeptide as it exists in *N. meningitidis*, or an antigenic, preferably immunogenic, fragment of the whole polypeptide. Antigenic and/or immunogenic fragments of antigenic and/or immunogenic polypeptides may be identified by methods known in the art. Usually, the antigenic fragment will comprise at least a portion of the segment having an amino acid sequence that is different from, but homologous to, the amino acid sequence of a segment of a polypeptide that is a member of the hemolysin family of toxins, or will comprise at least a portion of the segment having at least three, preferably at least five, and more preferably at least ten hemolysin consensus sequences.

Preparation of the Polypeptide

The polypeptides of the present invention may be prepared by methods known in the art. Such methods include isolating the polypeptide directly from *N. meninaitidis*; isolating or synthesizing DNA encoding the polypeptide and using the DNA to produce recombinant polypeptide; and synthesizing the polypeptide from individual amino acids.

The polypeptide or DNA encoding the polypeptide may be isolated from any serotype of *N. meningitidis*. Such serotypes include A, B, C, D, X, Y, Z, 29-E and W-135.

Suitable sources of meningococcal strains from which the polypeptide and DNA encoding the polypeptide may be isolated are available. Such sources include the American Type Culture Collection (Bethesda, Md.) and the Neisseria Repository (NAMRU, University of California, Berkeley). Suitable strains include FAM18 and FAM20 (Dyer et al, Microbial Pathogenesis 3, 351–363 (1987)), and FAM 19. Additional meningococcal strains are described by Schryvers and Morris in Infection and Immunity 56, 1144–1149 (1988).

The polypeptide may be isolated directly from *N. meningitidis* by methods known in the art. First, meningococcal outer membranes are isolated and prepared by known methods. The methods described by West and Sparling in Infect. Immun. 47, 388–394 (1985) and by Schryvers and Morris in Infect. Immun. 56, 1144–1149 (1988) are suitable.

The isolated membrane proteins may be solubilized by known methods, such as the addition of detergents. Commonly used detergents include Octyl-B-Glucoside, Chaps, Zwittergent 3.14 or Triton-X. The use of detergents to enhance solubility of membrane proteins is described by Jones et al. in Finby, Solubilization and Reconstitution of Membrane Proteins: A Practical Approach, IRL Press (1986), Helenius et al. in Biochim. Biophys. Acta 415, 29 (1975) and Hjelmeland and Chrambach, Methods Enzymol. 104, 305 (1984).

Proteins are isolated from the solubilized membrane fraction by standard methods. Some suitable methods include precipitation and liquid chromatographic protocols such as ion exchange, hydrophobic interaction and gel filtration. See, for example, Methods Enzymol. 182 (Guide to Protein Chemistry, Deutscher, Ed. Section VII) 309 (1990) and Scopes, Protein Purification. Springer-Verlag, New York (1987).

Alternatively, purified material is obtained by separating the protein on preparative SDS-PAGE gels, slicing out the band of interest and electroeluting the protein from the polyacrylamide matrix by methods known in the art. The detergent SDS is removed from the protein by known methods, such as by dialysis or the use of a suitable column, such as the Extracti-Gel column from Pierce.

The polypeptide may also be produced by isolating DNA that encodes the polypeptide; cloning the DNA in a suitable host; expressing the DNA in the host; and harvesting the polypeptide.

The first DNA encoding the polypeptide of the present invention was isolated by an immunoscreening method. Such methods are described by Maniatis et al in "Molecular Cloning: A Laboratory Manual," Cold Spring Harbor Laboratory Press, Cold Spring Harbor, N.Y. (1982).

Briefly, monoclonal antibodies were generated against iron-stressed outer membrane proteins of *N. meningitidis* strain FAM20. One monoclonal antibody, A4.85, recognized several iron-regulated proteins in Western blots of the FAM20 outer membranes. A4.85 was used to isolate a clone from an FAM20 genomic library constructed in the expression vector lambda-gt11. The sequence of this clone was determined and used to clone adjacent genomic restriction fragments. The adjoined DNA sequence of this region contained a long open reading frame, which is included in FIGS. 2A–G. See Seq. ID No. 1. The amino acid sequence predicted from the nucleotide sequence of FIGS. 2A–G is shown as FIGS. 3A–E. See Seq. ID No. 2.

A FASTA homology search in accordance with Pearson and Lipman, Proc. Natl. Acad. Sci. USA 85, 2444–2448 (1988) of the amino acid sequence deduced from the open reading frame (FIGS. 3A–E) was performed. Surprisingly, the amino acid sequence exhibited substantial homology to several members of the hemolysin family of toxins, as discussed above.

As further evidence that the polypeptide isolated from *N. meningitidis* is a member of the hemolysin family of toxins, the antibody raised against, and used to isolate, the polypeptide shown as FIGS. 3A–E (See Seq. ID No. 2.), A4.85, cross-reacted strongly with alpha-hemolysin (HlyA) from *E. coli* and with adenylate cyclase produced in *Bordetella pertussis.*

The immunoscreening method may be repeated in order to obtain additional fragments of the gene encoding the polypeptide of the invention or to obtain the gene encoding the entire polypeptide. It is, of course, not necessary to repeat the immunoscreening process. The entire gene or additional fragments of the gene are preferably isolated by using the known DNA sequence or fragments thereof as a probe. To do so, meningococcal DNA restriction fragments, either flanking the ends of the region already cloned or containing the entire region, are identified by Southern hybridization using labelled oligonucleotide probes derived from a previously determined sequence, such as that shown as FIGS. 2A–G, or a fragment thereof. See Seq. ID No. 1.

The DNA obtained may be amplified by methods known in the art. One suitable method is the polymerase chain reaction (PCR) method described by Mullis et al in U.S. Pat. No. 4,683,195 and by Sambrook, Fritsch and Maniatis (eds) in *Molecular Cloning, A Laboratory Manual*, Second Edition, Cold Spring Harbor Laboratory Press (1989). It is convenient to amplify the clones in the lambda-gt11 vectors using lambda-gt11-specific oligomers as the amplimers (available from New England Biolabs, Beverly, Ma.).

The restriction fragments are cloned into a suitable vector, such as a plasmid or bacteriophage, and sequenced in accordance with methods known in the art. A suitable sequencing method is the dideoxy chain terminating method described by Sanger et al in Proc. Natl. Acad. Sci. USA 74, 5463–5467 (1977). Suitable vectors and polymerases for sequencing are known. A suitable vector is the lambda-gt11 specific primer. (New England Biolabs, Beverly, Ma.). A suitable polymerase is Sequenase (United States Biochemical Corp., Cleveland, Ohio).

The DNA encoding the polypeptide of the invention may be used to express recombinant polypeptide in a wide variety of host cells using a wide variety of vectors. The host may be prokaryotic or eukaryotic. The DNA may be obtained from natural sources and, optionally, modified. The genes may also be synthesized in whole or in part.

Cloning vectors may comprise segments of chromosomal, non-chromosomal and synthetic DNA sequences. Some suitable prokaryotic vectors include plasmids from *E. coli*, such as colE1, pCR1, DBR322, pMB9, and RP4. Prokaryotic vectors also include derivatives of phage DNA such as M13, f1, and other filamentous single-stranded DNA phages.

Vectors for expressing proteins in bacteria, especially *E.coli*, are also known. Such vectors include pK233 (or any of the tac family of plasmids), T7, and lambda $P_L$. Examples of vectors that express fusion proteins include the PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. Other expression vector systems are based on beta-galactosidase (pEX); maltose binding protein (pMAL); and glutathione S-transferase (pGST)—see Gene 67, 31 (1988) and Peptide Research 3, 167 (1990).

Vectors useful in yeast are available. A suitable example is the 2μ plasmid.

Suitable vectors for use in mammalian cells are also known. Such vectors include well-known derivatives of SV-40, adenovirus, retrovirus-derived DNA sequences and vectors derived from combination of plasmids and phage DNA.

Further eukaryotic expression vectors are known in the art (e.g., P. J. Southern and P. Berg, J. Mol. Appl. Genet. 1, 327–341 (1982); S. Subramani et al, Mol. Cell. Biol. 1, 854–864 (1981); R. J. Kaufmann and P. A. Sharp, "Amplification And Expression Of Sequences Cotransfected with A Modular Dihydrofolate Reductase Complementary DNA Gene," J. Mol. Biol. 159, 601–621 (1982); R. J. Kaufmann and P. A. Sharp, Mol. Cell. Biol. 159, 601–664 (1982); S. I. Scahill et al, "Expression And Characterization Of The Product Of A Human Immune Interferon DNA Gene In Chinese Hamster Ovary Cells," Proc. Natl. Acad. Sci. USA 80, 4654–4659 (1983); G. Urlaub and L. A. Chasin, Proc. Natl. Acad. Sci. USA 77, 4216–4220, (1980).

Useful expression hosts include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRCl, Pseudomonas, Bacillus, such as *Bacillus subtilis*, and Streptomyces. Suitable eukaryotic cells include yeasts and other fungi, insect, animal cells, such as COS cells and CHO cells, human cells and plant cells in tissue culture.

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the try system, the tac system, the trc system, major operator and promoter regions of phage lambda, the control region of f1 coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The recombinant polypeptide is purified by methods known in the art. Suitable methods are described F. A. O. Marston, "The Purification of Eukaryotic Polypeptides Expressed in *Escherichia coli*," in *DNA Cloning*, D. M. Glover, Ed., Vol. III, IRL Press Limited, England (1987).

The polypeptide of the invention and DNA encoding the polypeptide may also be chemically synthesized from individual amino acid residues and nucleotides, respectively, by methods known in the art. Suitable methods for synthesizing the polypeptide are described by Stuart and Young in "Solid Phase Peptide Synthesis," Second Edition, Pierce Chemical Company (1984). Suitable methods for synthesizing DNA are described by Caruthers in Science 230, 281–285 (1985).

Vaccines

A polypeptide comprising a segment having an amino acid sequence that is different from, but substantially homologous with, the amino acid sequence of a member of the hemolysin family of toxins is, unexpectedly, an antigen useful for protecting a mammal from infectious diseases caused by *N. Meningitidis*. The mammal is typically a human.

To be useful, the antigen is non-toxic to the mammal being immunized. If the antigen is toxic, it may be detoxified by methods known in the art. Such methods include, for example, providing antigenic, non-toxic fragments of the entire polypeptide or detoxifying a polypeptide by, for example, binding the toxin to a carrier molecule that destroys toxicity, but does not affect antigenicity. The carrier molecule is typically another polypeptide.

Preferably, an amino acid sequence of the antigen is present in a polypeptide found in *N. meningitidis*. The polypeptide or non-toxic, antigenic fragments useful in immunizing mammals may be made by methods known in the art, such as by isolation from *N. meningitidis*, production by recombinant DNA techniques, or chemical synthesis, as described above.

The length of the fragment is not critical as long as the fragment is antigenic and non-toxic. Therefore, the fragment should contain sufficient amino acid residues to define the epitope. Methods for isolating and identifying antigenic fragments from known antigenic polypeptides are described by Salfeld et al. in J. Virol. 63, 798–808 (1989) and by Isola et al. in J. Virol. 63, 2325–2334 (1989).

If the fragment defines the epitope, but is too short to be antigenic, it may be conjugated to a carrier molecule. Some suitable carrier molecules include keyhole limpet hemocyanin and bovine serum albumen. Conjugation may be carried out by methods known in the art. One such method is to combine a cysteine residue of the fragment with a cysteine residue on the carrier molecule.

The present invention further includes vaccine compositions for immunizing mammals, including humans, against infection by *N. meningitidis*. The vaccine comprises an immunogenic antigen as described above in a suitable carrier. Suitable carriers include any of the standard pharmaceutically acceptable carriers, such as water, phosphate buffered saline solution, and emulsions.

The vaccine may include adjuvants, such as muramyl peptides, and lymphokines, such as interferon, interleukin-1 and interleukin-6. The antigen may be adsorbed on suitable particles, such as aluminum oxide particles, or encapsulated in liposomes, as is known in the art.

The invention further includes methods of immunizing host mammals, including humans, by administering the vaccine compositions described above to mammals in need of protection from diseases caused by *N. meningitidis*. The vaccine comprises an immunogenic polypeptide in a form that is non-toxic to mammals. The polypeptide comprises an amino acid sequence that is homologous with the amino acid sequence of a member of the hemolysin family of toxins.

The amino acid sequence is preferably present in *N. meningitidis*, and is usually found in the outer membranes of *N. meningitidis*. Since, however, antibodies cross-react with the polypeptide of the invention and members of the hemolysin family of toxins from other genera of bacteria, the antigen in the vaccine composition may comprise an amino acid sequence in such other genera, such as from *E. coli* or *B. pertussis*.

The vaccine may be administered to a mammal by methods known in the art. Such methods include, for example, intravenous, intraperitoneal, subcutaneous, or intramuscular administration.

Antibodies

The present invention provides antibodies raised against a polypeptide of the invention. The polypeptide comprises an amino acid sequence that defines an epitope, and is substantially homologous with the amino acid sequence of a member of the hemolysin family of toxins. The antibodies are preferably raised against a polypeptide comprising an amino acid sequence that is present in *N. Meningitidis*, and that is different from polypeptides that are members of the hemolysin family of toxins from other genera of bacteria.

The antibodies are preferably monoclonal. Monoclonal antibodies may be produced by methods known in the art. These methods include the immunological method described by Kohler and Milstein in Nature 256, 495–497 (1975) and the recombinant DNA method described by Huse et al in Science 246, 1275–1281 (1989).

Mammals, including humans, suffering from diseases caused by infection with *N. meningitidis* may be treated by administering antibodies specific to a member of the hemolysin family of toxins. Antibodies raised against a member of the hemolysin family of toxins from any genera of bacteria are suitable, although antibodies raised against a polypeptide comprising an amino acid sequence present in *N. meningitidis* is preferred.

For therapeutic purposes, it is necessary for the antigenic polypeptides of the invention to produce neutralizing antibodies. Neutralizing antibodies are antibodies that significantly inhibit the growth of or kill the bacterial cells and/or significantly neutralize the toxin function of the polypeptide in vitro or in vivo. Growth of the bacteria is significantly inhibited or the toxin function of the polypeptide is significantly neutralized in vivo if the inhibition or neutralization is sufficient to prevent or reduce the symptoms of the disease of a mammal infected with the disease.

Neutralizing antibodies may also be used to produce anti-idiotypic antibodies useful as vaccines for immunizing mammals, including humans, suffering from diseases caused by infection with *N. meningitidis*. Anti-idiotypic antibodies are prepared in accordance with methods known in the art.

Nucleic Acid Molecules

The present invention also includes isolated nucleic acid molecules that encode any of the polypeptides of the invention described above. The nucleic acid molecule may be DNA or RNA.

The utility of the nucleic acid molecule lies in its ability to be used as a probe for detecting *N. meningitidis*, as explained below, or to produce a polypeptide of the invention, as explained above. The nucleic acid molecule may be prepared by methods known in the art. Suitable methods include isolating the DNA from *N. Meninaitidis* or synthesizing the DNA in accordance with known procedures as described above.

Probes

The present invention further provides a method of detecting the presence of *N. meningitidis* in a sample. The method involves use of a probe that recognizes a polypeptide that is a member of the hemolysin family of toxins, and, in particular, a member of the hemolysin family of toxins present in *N. meningitidis*, or a gene encoding such a polypeptide. The probe recognizes *N. meningitidis* if present in the sample.

The probe may be an antibody, preferably a monoclonal antibody. The antibodies may be prepared as described above.

Methods are known for detecting polypeptides with antibodies. For example, a polypeptide may be immobilized on a solid support. Immobilization of the polypeptide may occur through an immobilized first antibody specific for the polypeptide. The immobilized first antibody is incubated with a sample suspected of containing the polypeptide. If present, the polypeptide binds to the first antibody.

A second antibody, also specific for the polypeptide, binds to the immobilized polypeptide. The second antibody may be labelled by methods known in the art. Non-immobilized materials are washed away, and the presence of immobilized label indicates the presence of the polypeptide. This and other immunoassays are described by David, et al., in U.S. Pat. No. 4,376,110 assigned to Hybritech, Inc., La Jolla, Calif.

The probe may also be a nucleic acid molecule that recognizes a RNA or DNA molecule that encodes a member of the hemolysin family of toxins present in *N. meningitidis*. Methods for determining whether a nucleic acid molecule probe recognizes a specific nucleic acid molecule in a sample are known in the art. Generally, a labelled probe that is complementary to a nucleic acid sequence suspected of being in a sample is prepared. The presence of probe hybridized to the target nucleic acid molecule indicates the presence of the nucleic acid molecule. Suitable methods are described by Schneider et al in U.S. Pat. No. 4,882,269, which is assigned to Princeton University, and by Segev in PCT Application WO 90/01069. The Schneider et al patent and the Segev application are both licensed to ImClone Systems Inc., New York City.

The probes described above are labelled in accordance with methods known in the art. Methods for labelling antibodies have been described, for example, by Hunter and Greenwood in Nature 144, 945 (1962) and by David et al in Biochemistry 13, 1014–1021 (1974). Additional methods for labelling antibodies have been described in U.S. Pat. Nos. 3,940,475 and 3,645,090. Methods for labelling oligonucleotide probes have been described, for example, by Leary et al, Proc. Natl. Acad. Sci. USA (1983) 80:4045; Renz and Kurz, Nucl. Acids Res. (1984) 12:3435; Richardson and Gumport, Nucl. Acids Res. (1983) 11:6167; Smith et al, Nucl. Acids Res. (1985) 13:2399; and Meinkoth and Wahl, Anal. Biochem. (1984) 138:267.

The label may be radioactive. Some examples of useful radioactive labels include $^{32}P$, $^{125}I$, $^{131}I$, and $^{3}H$. Use of radioactive labels have been described in U.K. 2,034,323, U.S. Pat. No. 4,358,535, and U.S. Pat. No. 4,302,204.

Some examples of non-radioactive labels include enzymes, chromophors, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman, Proc. Natl. Acad. Sci., 47, 1981–1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the antibody or nucleotide probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate.

The label may also be conjugated to the probe by means of a ligand attached to the probe by a method described above and a receptor for that ligand attached to the label. Any of the known ligand-receptor combinations is suitable. The biotin-avidin combination is preferred.

The polypeptide of the invention may be used to detect the presence of antibodies specific for *N. meningitidis* in a sample. The method comprises preparing a polypeptide containing a segment having an amino acid sequence that is substantially homologous to a member of the hemolysin family of toxins. The polypeptide may be prepared as described above. Preferably, the polypeptide comprises a segment having an amino acid sequence that is present in *N. meningitidis.*

The sample may, for example, be from a patient suspected of being infected with *N. meningitidis*. Suitable assays are known in the art, such as the standard ELISA protocol described by R. H. Kenneth, "Enzyme-Linked Antibody Assay with Cells Attached to Polyvinyl Chloride Plates" in Kenneth et al, *Monoclonal Antibodies*, Plenum Press, N.Y., page 376 (1981).

Briefly, plates are coated with antigenic polypeptide at a concentration sufficient to bind detectable amounts of the antibody. After incubating the plates with the polypeptide, the plates are blocked with a suitable blocking agent, such as, for example, 10% normal goat serum. The sample, such as patient sera, is added and titered to determine the endpoint. Positive and negative controls are added simultaneously to quantitate the amount of relevant antibody present in the unknown samples. Following incubation, the samples are probed with goat anti-human Ig conjugated to a suitable enzyme. The presence of anti-polypeptide antibodies in the sample is indicated by the presence of the enzyme.

Antibodies raised against polypeptides of the present invention are capable of recognizing *N. meningitidis* and distinguishing meningococcal cells from gonococcal cells in a sample. The A4.85 monoclonal antibody, for example, recognizes a polypeptide expressed by iron-stressed meningococcal cells. A4.85 does not, however, recognize any proteins in iron-stressed *N. gonorrhoeae.*

The antibodies may be labelled by known methods as described above. Assays for distinguishing iron-stressed meningococcal cells from iron-stressed gonococcal cells follow known formats, such as standard blot and ELISA formats.

EXAMPLES

Example 1

Isolation of A4.85 MAb

Bacterial outer membranes are prepared from iron-stressed cultures of *Neisseria meningitidis* strain FAM20 as follows. FAM20 is inoculated into chelexed defined medium (CDM, West et al, J. Bacteriology 169, 3414 (1987)). This medium allows growth only until iron stores within the bacteria have been depleted. During this time, a set of proteins that are regulated by the availability of iron become expressed. Bacteria are harvested and outer membranes are prepared as described by Dyer et al in Infection and Immunity 56, 977 (1988).

Three to five BALB/c female mice are immunized with iron-stressed FAM20 outer membranes by either the intramuscular (im) or intraperitoneal (ip) routes. With the im route, 100 $\mu$g of antigen (Ag) is emulsified in complete Freund's adjuvant and injected on two different sites on day zero, followed by booster doses two weeks apart with the Ag now emulsified in incomplete Freund's adjuvant. The ip route involves immunization with 100 $\mu$g of Ag on days zero, 7, 14 and 28. Serum antibody levels are checked by either ELISA or Western blotting three days following the final boost to determine serum antibody levels. Mice are given a final boost ip on each of three consecutive days before the fusion. On the day of the fusion, mice are sacrificed by cervical dislocation and the spleens are removed aseptically. Spleen cells are extracted by teasing the cells out of the sac using two bent 19 ga needles. Extracted cells are resuspended to give single cell suspensions.

Mouse myeloma cells, SP2.0-AG14 (ATCC CRL 1581), that have been grown in Dulbecco's Modified Eagle's Medium/Ham's F-12 (DMEM/F12) supplemented with 15% fetal calf serum (FCS), are used as the fusion partner. Cells are mixed in a 10:1 ratio of spleen:myeloma cells and pelleted together in a 50 ml centrifuge tube. The supernatant is aspirated off leaving a dry pellet to which 1 ml of 50% polyethylene glycol (PEG) (prewarmed to 37° C.) is added. The cells are gently resuspended and allowed to sit at room temperature for 2 minutes, after which 1 ml of DMEM/F12 without added sera is added and the cells gently resuspended. The cells are then further diluted and resuspended with 2, 4, 8 and 16 ml of DMEM/F12 added at two-minute intervals. The cells are then pelleted and the supernatant aspirated. Two ml of DMEM/F12 supplemented with 15% FCS is carefully added to avoid resuspension of the pellet and then incubated for one hour at 37° C.

At the end of the 1 hour incubation, the suspension is diluted to a final concentration of $1\times10^6$ cells/ml. This suspension is then poured into tissue culture flasks and incubated overnight. The next day an equal volume of culture media supplemented with 2X HAT (hypoxanthine, aminopterin, thymidine) components are plated out into 96-well plates with 200 $\mu$l/well with $1\times10^5$ spleen cells/well. Plated cells are fed every 4–5 days after the fusion by aspiration of half the media from the wells and addition of fresh 1×HAT media. The wells are scored for growth after 10–14 days, and growing wells are tested for presence of secreted antibody by screening the culture supernatants by either an ELISA or Western blotting. Wells that prove positive on assay are expanded for growth into 24-well culture dishes in culture media with HT supplements (no aminopterin) and re-tested. Those proving positive on re-testing are expanded further into larger tissue culture vessels and then cloned twice by limiting dilution.

A cell line (A4.85) that arose from a single mouse spleen cell was isolated. A4.85 produces a monoclonal antibody (Mab) that reacts with several protein species (70 kilodaltons to several hundred kilodaltons in mass) on a Western blot of FAM20 outer membranes, each of whose synthesis is repressed by the presence of iron in the bacterial growth medium.

Example 2A

Isolation of Genomic Clones

A. Library Construction

A library of *Neisseria meningitidis* strain FAM20 chromosomal DNA is constructed in the bacteriophage vector lambda-gt11 as follows. FAM20 chromosomal DNA is isolated by standard methods (Maniatis et al, 1982). The DNA is sheared by sonication to fragment sizes of approximately 300–1000 bp. Synthetic EcoRI linkers are ligated to the ends of these molecules, followed by cleavage with EcoRI restriction endonuclease to generate EcoRI restriction sites at the end of each molecule. The resulting fragments are ligated with EcoRI-cleaved lambda-gt11 DNA (Maniatis et al, Molecular Cloning: A Laboratory Manual, Cold Spring Harbor Laboratory Press, Cold Spring Harbor, N.Y. (1982)). The ligated DNA is packaged into lambda phage heads using lambda packaging extracts (Promega Corp., Madison, Wis.), according to manufacturer's instructions.

B. Library Screening and Isolation of DNA

The library created above is screened with the A4.85 Mab to detect clones that express the epitope recognized by A4.85. 500,000 recombinant plaques from the lambda-gt11 expression library are screened by the method of Maniatis et al (1982). A pure clone reacting with the A4.85 Mab is isolated by re-plating and screening the reactive plaque twice. The meningococcal insert DNA from the pure lambda clone (lambda 4.85) is amplified by the polymerase chain reaction (PCR) technique using a kit from Perkin-Elmer/Cetus. The PCR-amplified DNA is cloned into the sequencing vector M13mp19 (Maniatis et al, 1982) and the DNA sequence determined by the dideoxy chain termination method of Sanger et al (Proc. Natl. Acad. Sci. USA 74, 5463–5467 (19877)) using the Sequenase kit (Stratagene, La Jolla, Calif.).

The cloned meningococcal DNA is labelled with $^{32}$P by the random primed method with a kit from Boehringer-Mannheim (Indianapolis, Ind.) and is used in Southern hybridizations (Maniatis et al, 1982) to identify DNA restriction fragments in the FAM20 chromosome adjacent to the DNA cloned in lambda 4.85. Chromosomal Sau3A I fragments of approximately 560 and 1600 bp hybridize to the cloned meningococcal DNA. FAM20 DNA is cleaved with Sau3A I and fractionated on a preparative agarose gel. Two size fractions are isolated, one of 400–700 bp and one of 1400–1800 bp.

The 560 bp Sau3A I fragment is cloned by ligating the 400–700 bp fraction of FAM20-Sau3A I fragments with BamHI-cleaved plasmid PBR322 (Maniatis et al, 1982). The desired clones of the 560 bp fragment are identified by hybridization of bacterial colonies containing recombinant plasmids with $^{32}$P-labelled lambda 4.85 insert DNA (Maniatis et al, 1982). Plasmid DNA (pUNCH201) from a pure colony hybridizing with the DNA probe is prepared and its sequence determined using Sequenase as modified for use in double-strand sequencing (Kraft et al, BioTechniques 6, 544 (1988)). Southern hybridization is used to verify that the cloned fragment is representative of the fragment intact in the FAM20 genome.

To clone the 1600 bp fragment, the ends of the 1400–1800 bp fraction of FAM20-Sau3A I fragments are made blunt by reaction with Klenow enzyme and DNA nucleotides. Synthetic EcoRI linkers are added to these molecules, followed by ligation with EcoRI-cleaved, alkaline-phosphatase-treated lambda ZAP DNA (Stratagene, LaJolla, Calif.) in accordance with technical information supplied with the lambda ZAP kit. Ligated DNA is packaged into lambda heads using Packagene lambda packaging extracts (Promega). The library of 1400–1800 bp FAM20-Sau3A I fragments is screened with a $^{32}$P-labelled oligonucleotide (SAT1), which is synthesized to correspond to DNA sequences at one end of the lambda 4.85 insert (5' GCCAT-TGCCACTGTAGATA 3'). A lambda ZAP plaque hybridizing with the SAT1 oligonucleotide is purified as above. The interior portion of this lambda ZAP clone (lambda ZAP202) is "excised" by the addition of helper bacteriophage. The excision results in a multicopy plasmid (pUNCH202) containing the cloned meningococcal insert. Southern hybridization is used to verify that the cloned fragment is representative of the fragment intact in the FAM20 genome. The sequence of the cloned DNA fragment is determined by double-strand sequencing as described above.

To obtain the entire DNA sequence of the gene for an antigenic iron repressible protein (frpA) from *N. meningitidis* related to the hemolysin family of toxins, two additional clones, pUNCH206 and pUNCH210, are isolated. These clones contain fragments flanking pUNCH201 and represent the entirety of the frpA gene.

To isolate pUNCH206, a 2.7 kilobase (kb) EcoRI to HincII fragment overlapping pUNCH201 is cloned as follows. FAM20 chromosomal DNA is digested to completion with HincII. EcoRI linkers are ligated to the ends of these fragments, which are then ligated to EcoRI-digested lambda ZAP. The desired clone is identified by hybridization with $^{32}P$-labelled pUNCH201 insert. The interior portion of this clone is "excised" by the addition of helper bacteriophage, and is designated pUNCH206. The pUNCH206 insert contains the 3' end of the frpA gene.

To obtain pUNCH210, a 4.3 kb SpeI to ClaI fragment overlapping the pUNCH206 insert is cloned as follows. FAM20 DNA is digested with SpeI and NheI, the fragments are separated by pulsed-field gel electrophoresis using a CHEF apparatus and are transferred to a BA-S85 membrane. (Schleicher & Schuell, Keene, N.H.).

The fragment of interest is identified by hybridization. This fragment is electrophoresed from the gel onto DE81 DEAE-cellulose paper and purified. This DNA is digested with ClaI and the ends made blunt by treatment with Klenow enzyme and DNA nucleotides. This is ligated with lambda ZAP which had been digested with EcoRI, then treated with Klenow fragment. The desired clone is identified by hybridization with $^{32}P$-labelled pUNCH210 insert. The interior portion of this clone is "excised" by the addition of helper bacteriophage, and is designated pUNCH210. The pUNCH210 insert contains the 5' end of the frpA gene.

The adjoined sequence of pUNCH210 and pUNCH206 reveals the presence of an open reading frame that contains the entirety of the cloned DNA. The DNA sequence is included in FIGS. 2A–G. See Seq. ID No. 1. The amino acid sequence predicted by the sequence contains 1115 amino acids. The putative amino acid sequence is shown as FIGS. 3A–E. See Seq. ID No. 2. The relationship to one another of the above-described restriction fragments is shown in FIG. 1.

As determined by FASTA sequence comparison searches (see above), both the DNA and the deduced polypeptide sequence from this region have a high degree of similarity with a family of hemolysin bacterial toxins. For example, the DNA sequence shown in FIGS. 2A–G (Seq. ID No. 1.) exhibits 54% identity with the cya gene (adenylate cyclase)

from *B. pertussis*; 60% identity with the hlyA, hlyB, hlyC and hlyD gene from *E. coli* (hemolysin); 65% identity with hlyA, hlyB and hlyC gene (hemolysin) from *E. coli*; 56% identity with the leukotoxin gene from *A. actinomycetemcomitans*; 56% identity with the hemolysin gene from *A. pleuropneumoniae*; 60% identity with the leukotoxin gene from *P. haemolytica*; 62% identity with the A1 leukotoxin gene from *P. Haemolytica*; and 57% identity with protease B gene of *E. chrysanthemi*.

The amino acid sequence predicted from the DNA sequence exhibited 25%–28% identity with leukotoxin, 22%–28% identity with hemolysin; and 30% identity with adenylate cyclase.

Meningococcal strain FAM20 contains at least two copies of DNA that encode the polypeptides of the invention. This can be demonstrated by digesting genomic DNA with the infrequent cutters BglII, SpeI, NheI, and combinations of NheI and SpeI. Southern blots of the digested DNA separated by pulse field gradient electrophoresis reveal two major bands that hybridize under stringent conditions to gene probes containing fragments of the sequence of the gene that encodes the polypeptide of the invention.

The remainder of the gene encoding the iron-regulated polypeptide of the invention is isolated in a manner similar to that described above for isolating pUNCH201 and pUNCH202. DNA restriction fragments either flanking the ends of the region already cloned or containing the entire region are identified by Southern hybridization using oligonucleotide probes derived from previously determined DNA sequence. These fragments are cloned into either plasmid or bacteriophage vectors as described above for pUNCH201 and pUNCH202. The DNA sequence of newly cloned fragments is determined as above, and reveals when either end of the gene is reached. If the gene is isolated on a single DNA fragment, it is expressed in an in vitro assay to verify that the protein that is encoded by this gene reacts with the A4.85 Mab. If the gene is not cloned intact on a single DNA fragment, it is reconstructed through standard molecular biology techniques to yield the intact gene (Carbonetti, Proc. Natl. Acad. Sci. USA 84, 9084 (1987)).

For example, DNA fragments from one of the two copies of the structural genes coding for the polypeptide of the invention were purified from agarose gels, cloned and sequenced. FIGS. 2A–G includes the DNA sequence. See Seq. ID No. 1.

Example 2B
Western Blot and Molecular Weight

The full length polypeptide obtained from meningococcal strain FAM20 exhibits a molecular weight of 230–250 kD when subjected to Western blot analysis. Western blots may be carried out as follows:

Iron-starved whole cells of FAM20 are prepared in accordance with the method of West and Sparling, J. Bacteriol. 169, 3414–3421 (1987). The cells are washed in ice-cold Davis Minimal Medium A (Lederberg, Methods in Med. Res., 3:5 (1950)), immediately cooled on ice, and ruptured in a French pressure cell at 0° C. and 20,000 psi. The resulting mixture is centrifuged for 10 minutes at 20,000 G, and the pellet solubilized in boiling SDS. The solubilized membrane proteins are separated by standard 7.5% SDS-PAGE in Laemli buffer, which was described by Laemli in Nature 227, 680–685 (1970). The proteins are transferred (16 hours, 80 $\mu$A) onto Optibind nitrocellulose membranes (available from Schleicher & Schuell). The membranes are blocked for 1 hour in 5% BSA in TBS (20 mM Tris, 500 Mm NaCl, pH 7.5); rinsed for 5 minutes in TBS; incubated for 1 hour with 1:2 dilution of monoclonal antibody A4.85 (see above) in 5% BSA; washed twice for 5 minutes in TBS and 0.05% Tween 20; incubated for 1 hour in a secondary antibody (goat anti-mouse IgG alkaline phosphatase conjugate) diluted in 5% BSA, available from BioRad (dilution=1:3000) or Sigma (dilution=1:1000); washed twice for 5 minutes in TBS/Tween; washed again for 5 minutes in TBS; and developed with an alkaline phosphatase substrate comprising 45 $\mu$l Nitro Blue Tetrazolin, available from Sigma (75 mg/ml); 35 $\mu$l 5-bromo-4-chloro-3-indolylphosphate, p-tolnidine salt (50 mg/ml) in 10 ml of carbonate buffer, pH 9.8 (0.1 M NaHCO$_3$; 1 mM Mgcl$_2$).

Example 3

Assay for Antibody in Sample

A standard ELISA protocol is used to screen for the presence of antibodies against the polypeptide in proteins. Briefly, 96 well microtiter plates are coated with the antigen at concentrations varying from 50–100 ng per well in a high pH (9.6) carbonate buffer. The plates are incubated overnight at 9° C. and blocked with 10% normal goat serum for one hour at 37° C. Patient sera is added and titered to determine the endpoint. Control positive and negative sera is added at the same time to quantitate the amount of relevant antibody present in the unknown samples. After a 2–3 hour incubation at 37° C., samples are probed with goat anti-human Ig conjugated to horseradish peroxidase. Positive samples are determined by using TMB.

The invention as claimed is enabled in accordance with the specification and readily available references and starting materials. Nevertheless, the following cell lines have been deposited in the American Type Culture Collection, Bethesda, Md. on Jul. 12, 1990 in order to facilitate the making and using of the invention:

Meningococcal cell line FAM18 (Accession Number 55071)

Meningococcal cell line FAM20 (Accession Number 55072)

Hybridoma cell line A4.85 (Accession Number HB 10504) In addition, the following brochures containing useful protocols and information are available in the file history of this specification.

"Predigested Lambda Zap/Eco RI Cloning Kit Instruction Manual," Stratagene, La Jolla, Calif. (Nov. 20, 1987);

"Gigapack Plus" (for packaging recombinant lambda phage), Stratagene, La Jolla, Calif. (Apr. 25, 1988); and "picoBlue Immunoscreening Kit" Instruction Manual," Stratagene, La Jolla, Calif. (May 19, 1989).

What is claimed is:

1. An essentially pure polypeptide comprising the amino acid sequence shown in SEQ ID No. 2.

2. A method for detecting the presence of a polypeptide according to claim 1 in a sample suspected of containing the polypeptide, the method comprising the steps of:
   (a) contacting the sample with a labelled antibody that binds to the polypeptide; and
   (b) detecting the presence of the label bound to the polypeptide.

3. A method for detecting the presence of an antibody specific for the polypeptide according to claim 1 in a sample suspected of containing the antibody the method comprising the steps of:
   (a) immobilizing the polypeptide on a solid support;
   (b) contacting the sample with the immobilized polypeptide to bind any antibodies in the sample; and
   (c) detecting the presence of the bound antibody.

* * * * *

UNITED STATES PATENT AND TRADEMARK OFFICE
CERTIFICATE OF CORRECTION

PATENT NO.    : 6,086,896
DATED         : July 11, 2000
INVENTOR(S)   : Sparling et al.

It is certified that error appears in the above-identified patent and that said Letters Patent is hereby corrected as shown below:

<u>Title page,</u>
Item [73], now reads "Assignee: ImClone Systems Incorporated, New York, NY." should read -- Assignee: The University of North Carolina at Chapel Hill, Chapel Hill, NC. --

Signed and Sealed this

Third Day of December, 2002

JAMES E. ROGAN
*Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3758 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
      (A) ORGANISM: Neisseria meningitidis (ix) FEATURE:
      (A) NAME/KEY: CDS
      (B) LOCATION: 298..3645

(ix) FEATURE:
      (A) NAME/KEY: mat_peptide
      (B) LOCATION: 298..3642

(xi) SEQUENCE DESCRIPTION: SEQ ID NO:1:

```
TATATGTCTT TATTTGAATA TATCTTACGA TGGGGAAATA TTTATATATT TTATAATAAA     60

TTTTACTCAT TTGCTAATAT GTCATGGAAT ATTACTTGTA TTTTGTAGAA TTTTTCCATA    120

TGAAAATATT CCATTTACTA TTTTTCTGAA CTTTATTAGT TTATTTTTAA TATTTTTACC    180

TCTTATATTT ACCATAAGAG AGCTAATTGA TTCATATTAT ATTGAGTCGA TAATTAATTT    240

ATTCTTAATT TTAATTCCTC ACGTTATTTT TTTAATTTAC TTGAAAGGAA AGCAGAT       297

ATG ACA TCT GCA AAT TTT AAT ATT AAC GGT TTT GGA GAT GTG AAA TTA     345
Met Thr Ser Ala Asn Phe Asn Ile Asn Gly Phe Gly Asp Val Lys Leu
 1               5                  10                  15

ACA CCC TAT TCA CCA CTC TTG GGA TAT AAA GCT TGG GAT TCA TTT ATT     393
Thr Pro Tyr Ser Pro Leu Leu Gly Tyr Lys Ala Trp Asp Ser Phe Ile
                20                  25                  30

GGT TCT ATT CAA TCC TTA TCT GAT TTA ATC TAT AAT GTG GAT AAC AAT     441
Gly Ser Ile Gln Ser Leu Ser Asp Leu Ile Tyr Asn Val Asp Asn Asn
            35                  40                  45

AGA AAT AAA ATG GAA ATT ACT GTT AAT AAT GCT ATC CAA GCT GCA GAT     489
Arg Asn Lys Met Glu Ile Thr Val Asn Asn Ala Ile Gln Ala Ala Asp
     50                  55                  60

AGC TTT TTA AGC AGT ATT GGA AGA GAT AAC AAA ATA ACA AAT ACT GCT     537
Ser Phe Leu Ser Ser Ile Gly Arg Asp Asn Lys Ile Thr Asn Thr Ala
 65                  70                  75                  80

TCT TTA CTT GCA TCC CTC GAT AAC ATT TTT TTA AAT TTA AGA AAT GTA     585
Ser Leu Leu Ala Ser Leu Asp Asn Ile Phe Leu Asn Leu Arg Asn Val
                85                  90                  95

TCT CGA GAT ATA CGA GAA ACA GGA AAA TTT AAA CCT AAT GAT ATT CAA     633
Ser Arg Asp Ile Arg Glu Thr Gly Lys Phe Lys Pro Asn Asp Ile Gln
                100                 105                 110

CAA GCA ATT GGT GAT ATA TTC ATT GCT GCT GGT GAT GGA TTA CAA TAT     681
Gln Ala Ile Gly Asp Ile Phe Ile Ala Ala Gly Asp Gly Leu Gln Tyr
            115                 120                 125
```

-continued

| | |
|---|---|
| ATA AAA CAA CAA ACA GAG GCG ATG GCT CAA AGC AAA TTC TTA CCA ACT<br>Ile Lys Gln Gln Thr Glu Ala Met Ala Gln Ser Lys Phe Leu Pro Thr<br>130                             135                          140 | 729 |
| AAA TTA AAA ACT GGT TTA AAT GAT GTC CTT AAT TCT AGA ATG CTA AAA<br>Lys Leu Lys Thr Gly Leu Asn Asp Val Leu Asn Ser Arg Met Leu Lys<br>145                         150                         155                       160 | 777 |
| TCC TCT ACT GTT TTA CAG CAT GAA TTG AAT TAT TTG GGA TTT AAA ATA<br>Ser Ser Thr Val Leu Gln His Glu Leu Asn Tyr Leu Gly Phe Lys Ile<br>                         165                         170                       175 | 825 |
| AAG GAT TAT GGA AAC GAG AGG CTT GGC GAA TCT ATA ATG AAT ATA GAT<br>Lys Asp Tyr Gly Asn Glu Arg Leu Gly Glu Ser Ile Met Asn Ile Asp<br>               180                         185                       190 | 873 |
| GAT TTT ACA CCA AGT AAG ATA GCA AAC TTT TTT GCG GAT CCT GAT ACA<br>Asp Phe Thr Pro Ser Lys Ile Ala Asn Phe Phe Ala Asp Pro Asp Thr<br>         195                       200                       205 | 921 |
| TAC AGC AAT GTA TTA GAA GAA GTA TCT AGG TTT ATA TAT TCC TTA GTT<br>Tyr Ser Asn Val Leu Glu Glu Val Ser Arg Phe Ile Tyr Ser Leu Val<br>210                           215                       220 | 969 |
| CCT GAT GAT GCA AAC CCT TGG AAA GGG GGC GAA GAT TAT ATT GGA CGA<br>Pro Asp Asp Ala Asn Pro Trp Lys Gly Gly Glu Asp Tyr Ile Gly Arg<br>225                         230                       235                   240 | 1017 |
| GGG ATA AGT GAA TGG GGA GAG TTA CTG GAA AAA TGG TAT AAA CAA GAT<br>Gly Ile Ser Glu Trp Gly Glu Leu Leu Glu Lys Trp Tyr Lys Gln Asp<br>                    245                         250                   255 | 1065 |
| TTT CTC CCT TAT CTT GAA AAA GAA TGG GAC CAA TTT CCG AAA TTT GAA<br>Phe Leu Pro Tyr Leu Glu Lys Glu Trp Asp Gln Phe Pro Lys Phe Glu<br>             260                       265                       270 | 1113 |
| GAT TGG CTG CCT GAA TTC CCT GAA TGG GCA AGA GAG TGG TTG AAA TTA<br>Asp Trp Leu Pro Glu Phe Pro Glu Trp Ala Arg Glu Trp Leu Lys Leu<br>275                         280                       285 | 1161 |
| GAT CCC AAA CGT TCA GGC AAA TAT CAT GTC TAC GAC CCC CTC GCC CTA<br>Asp Pro Lys Arg Ser Gly Lys Tyr His Val Tyr Asp Pro Leu Ala Leu<br>         290                       295                       300 | 1209 |
| GAT CTA GAC GGC GAC GGT ATA GAA ACC GTT GCT GCC AAA GGC TTT GCA<br>Asp Leu Asp Gly Asp Gly Ile Glu Thr Val Ala Ala Lys Gly Phe Ala<br>305                         310                       315                   320 | 1257 |
| GGT GCA TTG TTC GAC CAC CGC AAT CAA GGC ATC CGC ACC GCC ACC GGT<br>Gly Ala Leu Phe Asp His Arg Asn Gln Gly Ile Arg Thr Ala Thr Gly<br>                         325                       330                     335 | 1305 |
| TGG GTT TCT GCC GAT GAC GGT TTA CTC GTC CGC GAT TTG AAC GGC AAC<br>Trp Val Ser Ala Asp Asp Gly Leu Leu Val Arg Asp Leu Asn Gly Asn<br>             340                       345                       350 | 1353 |
| GGC ATC ATC GAC AAC GGC GCG GAA CTC TTC GGC GAC AAC ACC AAA CTG<br>Gly Ile Ile Asp Asn Gly Ala Glu Leu Phe Gly Asp Asn Thr Lys Leu<br>355                         360                       365 | 1401 |
| GCA GAC GGT TCT TTT GCC AAA CAC GGC TAT GCA GCT TTG GCC GAA TTG<br>Ala Asp Gly Ser Phe Ala Lys His Gly Tyr Ala Ala Leu Ala Glu Leu<br>         370                       375                       380 | 1449 |
| GAT TCA AAC GGC GAC AAC ATC ATC AAC GCG GCA GAC GCC GCA TTC CAA<br>Asp Ser Asn Gly Asp Asn Ile Ile Asn Ala Ala Asp Ala Ala Phe Gln<br>385                         390                       395                   400 | 1497 |
| ACC CTG CGT GTA TGG CAG GAT CTC AAC CAG GAC GGC ATT TCC CAA GCT<br>Thr Leu Arg Val Trp Gln Asp Leu Asn Gln Asp Gly Ile Ser Gln Ala<br>             405                       410                       415 | 1545 |
| AAT GAA TTG CGT ACC CTT GAA GAA TTG GGT ATC CAA TCT TTG GAT CTC<br>Asn Glu Leu Arg Thr Leu Glu Glu Leu Gly Ile Gln Ser Leu Asp Leu<br>                    420                       425                   430 | 1593 |
| GCC TAT AAA GAT GTA AAT AAA AAT CTC GGT AAC GGT AAC ACT TTG GCT<br>Ala Tyr Lys Asp Val Asn Lys Asn Leu Gly Asn Gly Asn Thr Leu Ala<br>435                         440                       445 | 1641 |

```
CAG CAA GGC AGC TAT ACC AAA ACA GAC GGT ACA ACC GCA AAA ATG GGG      1689
Gln Gln Gly Ser Tyr Thr Lys Thr Asp Gly Thr Thr Ala Lys Met Gly
        450                 455                 460

GAT TTA CTT TTA GCA GCC GAC AAT CTG CAC AGC CGC TTC AAA GAC AAA      1737
Asp Leu Leu Leu Ala Ala Asp Asn Leu His Ser Arg Phe Lys Asp Lys
465                 470                 475                 480

GTG GAA CTC ACT GCC GAA CAG GCA AAA GCC GCC AAT CTT GCG GGC ATC      1785
Val Glu Leu Thr Ala Glu Gln Ala Lys Ala Ala Asn Leu Ala Gly Ile
                485                 490                 495

GGC CGT CTG CGC GAT TTG CGC GAA GCT GCC GCA TTG TCC GGC GAT TTG      1833
Gly Arg Leu Arg Asp Leu Arg Glu Ala Ala Ala Leu Ser Gly Asp Leu
            500                 505                 510

GCC AAT ATG CTG AAA GCT TAT TCT GCC GCC GAA ACT AAA GAA GCA CAG      1881
Ala Asn Met Leu Lys Ala Tyr Ser Ala Ala Glu Thr Lys Glu Ala Gln
        515                 520                 525

TTG GCA TTG TTA GAT AAT TTG ATT CAC AAA TGG GCG GAA ACC GAT TCG      1929
Leu Ala Leu Leu Asp Asn Leu Ile His Lys Trp Ala Glu Thr Asp Ser
530                 535                 540

AAC TGG GGC AAA AAA TCG CCA ATG CGA CTT TCA ACC GAT TGG ACG CAA      1977
Asn Trp Gly Lys Lys Ser Pro Met Arg Leu Ser Thr Asp Trp Thr Gln
545                 550                 555                 560

ACG GCT AAT GAA GGT ATT GCA CTG ACA CCA TCC CAA GTA GCA CAA CTA      2025
Thr Ala Asn Glu Gly Ile Ala Leu Thr Pro Ser Gln Val Ala Gln Leu
                565                 570                 575

AAA AAG AAC GCT TTA GTT TCC CTT TCT GAT AAA GCT AAA GCA GCT ATT      2073
Lys Lys Asn Ala Leu Val Ser Leu Ser Asp Lys Ala Lys Ala Ala Ile
            580                 585                 590

GAC GCC GCC CGC GAC CGC ATT GCC GTG CTT GAT GCC TAC ACG GGG CAG      2121
Asp Ala Ala Arg Asp Arg Ile Ala Val Leu Asp Ala Tyr Thr Gly Gln
        595                 600                 605

GAT TCC AGC ACA CTC TAT TAC ATG AGC GAA GAA GAC GCG CTT AAT ATC      2169
Asp Ser Ser Thr Leu Tyr Tyr Met Ser Glu Glu Asp Ala Leu Asn Ile
610                 615                 620

GTC AAA GTA ACC AAC GAT ACA TAC GAC CAT CTC GCC AAA AAC ATC TAC      2217
Val Lys Val Thr Asn Asp Thr Tyr Asp His Leu Ala Lys Asn Ile Tyr
625                 630                 635                 640

CAA AAC CTG TTG TTC CAA ACC CGT TTG CAG CCA TAT TTG AAT CAA ATC      2265
Gln Asn Leu Leu Phe Gln Thr Arg Leu Gln Pro Tyr Leu Asn Gln Ile
                645                 650                 655

AGT TTC AAA ATG GAA AAT GAT ACG TTC ACT TTG GAT TTT AGT GGT CTT      2313
Ser Phe Lys Met Glu Asn Asp Thr Phe Thr Leu Asp Phe Ser Gly Leu
            660                 665                 670

GTT CAA GCA TTT AAC CAT GTC AAA GAA ACT AAT CCG CAA AAA GCT TTT      2361
Val Gln Ala Phe Asn His Val Lys Glu Thr Asn Pro Gln Lys Ala Phe
        675                 680                 685

GTG GAT TTG GCC GAG ATG CTT GCA TAT GGC GAA CTT CGT TCT TGG TAT      2409
Val Asp Leu Ala Glu Met Leu Ala Tyr Gly Glu Leu Arg Ser Trp Tyr
690                 695                 700

GAA GGC CGA AGA CTA ATG GCC GAT TAT GTG GAG GAG GCA AAA AAA GCA      2457
Glu Gly Arg Arg Leu Met Ala Asp Tyr Val Glu Glu Ala Lys Lys Ala
705                 710                 715                 720

GGT AAA TTT GAA GAT TAC CAG AAA GTG TTG GGT CAG GAG ACC GTT GCA      2505
Gly Lys Phe Glu Asp Tyr Gln Lys Val Leu Gly Gln Glu Thr Val Ala
                725                 730                 735

TTA TTA GCT AAA ACA TCG GGT ACG CAA GCA GAT GAT ATC CTG CAA AAT      2553
Leu Leu Ala Lys Thr Ser Gly Thr Gln Ala Asp Asp Ile Leu Gln Asn
            740                 745                 750

GTA GGC TTT GGT CAT AAT AAA AAT GTT TCT TTA TAT GGT AAT GAC GGC      2601
Val Gly Phe Gly His Asn Lys Asn Val Ser Leu Tyr Gly Asn Asp Gly
```

```
                755                 760                 765
AAC GAC ACT CTA ATC GGC GGT GCA GGC AAT GAT TAC TTG GAG GGC GGC        2649
Asn Asp Thr Leu Ile Gly Gly Ala Gly Asn Asp Tyr Leu Glu Gly Gly
        770                 775                 780

AGC GGT TCG GAT ACT TAT GTC TTC GGC AAA GGC TTC GGT CAG GAT ACG        2697
Ser Gly Ser Asp Thr Tyr Val Phe Gly Lys Gly Phe Gly Gln Asp Thr
785                 790                 795                 800

GTC TAT AAT TAC GAC TAC GCT ACC GGA CGC AAA GAC ATC ATC CGC TTT        2745
Val Tyr Asn Tyr Asp Tyr Ala Thr Gly Arg Lys Asp Ile Ile Arg Phe
            805                 810                 815

ACC GAC GGT ATT ACA GCC GAT ATG CTG ACT TTT ACC CGA GAG GGC AAC        2793
Thr Asp Gly Ile Thr Ala Asp Met Leu Thr Phe Thr Arg Glu Gly Asn
        820                 825                 830

CAT CTT CTT ATC AAG GCA AAA GAC GAC AGT GGA CAA GTG ACT GTT CAG        2841
His Leu Leu Ile Lys Ala Lys Asp Asp Ser Gly Gln Val Thr Val Gln
            835                 840                 845

TCC TAT TTC CAG AAC GAT GGC TCA GGT GCT TAC CGT ATC GAT GAG ATT        2889
Ser Tyr Phe Gln Asn Asp Gly Ser Gly Ala Tyr Arg Ile Asp Glu Ile
        850                 855                 860

CAT TTC GAT AAC GGC AAA GTA CTG GAT GTT GCC ACT GTC AAA GAA CTG        2937
His Phe Asp Asn Gly Lys Val Leu Asp Val Ala Thr Val Lys Glu Leu
865                 870                 875                 880

GTA CAG CAA TCC ACC GAC GGT TCG GAC AGA TTG TAT GCC TAC CAA TCC        2985
Val Gln Gln Ser Thr Asp Gly Ser Asp Arg Leu Tyr Ala Tyr Gln Ser
            885                 890                 895

GGA AGT ACC TTA AAT GGC GGA TTG GGC GAT GAC TAT CTG TAC GGT GCC        3033
Gly Ser Thr Leu Asn Gly Gly Leu Gly Asp Asp Tyr Leu Tyr Gly Ala
        900                 905                 910

GAC GGG AAT GAC CTG CTG AAT GGT GAT GCA GGC AAC GAC AGT ATC TAC        3081
Asp Gly Asn Asp Leu Leu Asn Gly Asp Ala Gly Asn Asp Ser Ile Tyr
            915                 920                 925

AGT GGC AAT GGC AAT GAT ACG CTC GAT GGA GGA GAA GGC AAC GAC GCC        3129
Ser Gly Asn Gly Asn Asp Thr Leu Asp Gly Gly Glu Gly Asn Asp Ala
        930                 935                 940

CTG TAC GGC TAT AAT GGT AAC GAT GCA CTG AAT GGT GGC GAA GGC AAT        3177
Leu Tyr Gly Tyr Asn Gly Asn Asp Ala Leu Asn Gly Gly Glu Gly Asn
945                 950                 955                 960

GAT CAT TTG AAC GGC GAA GAC GGT AAC GAC ACT CTA ATC GGC GGT GCA        3225
Asp His Leu Asn Gly Glu Asp Gly Asn Asp Thr Leu Ile Gly Gly Ala
            965                 970                 975

GGC AAT GAT TAC TTG GAG GGC GGC AGC GGT TCG GAT ACT TAT GTC TTC        3273
Gly Asn Asp Tyr Leu Glu Gly Gly Ser Gly Ser Asp Thr Tyr Val Phe
        980                 985                 990

GGC GAA GGC TTC GGT CAG GAT ACG GTC TAT AAT TAC CAT GTG GAT AAA        3321
Gly Glu Gly Phe Gly Gln Asp Thr Val Tyr Asn Tyr His Val Asp Lys
            995                 1000                1005

AAC TCT GAC ACT ATG CAC TTT AAA GGA TTT AAA GCA GCA GAT GTT CAT        3369
Asn Ser Asp Thr Met His Phe Lys Gly Phe Lys Ala Ala Asp Val His
        1010                1015                1020

TTT ATC CGT TCC GGA AGT GAT TTG GTG CTT AGC GCT TCT GAA CAA GAC        3417
Phe Ile Arg Ser Gly Ser Asp Leu Val Leu Ser Ala Ser Glu Gln Asp
1025                1030                1035                1040

AAC GTA CGT ATT TCC GGA TTC TTC TAT GGT GAA AAC CAT CGT GTA GAT        3465
Asn Val Arg Ile Ser Gly Phe Phe Tyr Gly Glu Asn His Arg Val Asp
            1045                1050                1055

ACA TTT GTC TTT GAT GAT GCA GCT ATC AGT AAT CCA GAT TTT GCC AAG        3513
Thr Phe Val Phe Asp Asp Ala Ala Ile Ser Asn Pro Asp Phe Ala Lys
        1060                1065                1070

TAT ATT AAT GCT GGC AAT AAT TTG GTA CAG TCT ATG TCT GTG TTC GGT        3561
```

```
Tyr Ile Asn Ala Gly Asn Asn Leu Val Gln Ser Met Ser Val Phe Gly
         1075                1080                1085

TCT AAT ACT GCT GCG ACA GGA GGA AAT GTG GAT GCC AAT ATA CAA TCC         3609
Ser Asn Thr Ala Ala Thr Gly Gly Asn Val Asp Ala Asn Ile Gln Ser
         1090                1095                1100

GTA CAG CAG CCG TTA TTG GTA ACG CCA TCT GCA TAAGGAGCCT AATCACATTC      3662
Val Gln Gln Pro Leu Leu Val Thr Pro Ser Ala
1105                1110                1115

ATGGCTTAAA CTGAAAAACA GCAATCAAGT TTATTTTGAT TGCTGTTTTT CTTAATATTG       3722

GGATAAGGGT CGAGACCTTT GCAAAAATAG TCTGTT                                3758

(2) INFORMATION FOR SEQ ID NO:2:

(i) SEQUENCE CHARACTERISTICS:
        (A) LENGTH: 1115 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Ser Ala Asn Phe Asn Ile Asn Gly Phe Gly Asp Val Lys Leu
 1               5                  10                  15

Thr Pro Tyr Ser Pro Leu Leu Gly Tyr Lys Ala Trp Asp Ser Phe Ile
            20                  25                  30

Gly Ser Ile Gln Ser Leu Ser Asp Leu Ile Tyr Asn Val Asp Asn Asn
        35                  40                  45

Arg Asn Lys Met Glu Ile Thr Val Asn Asn Ala Ile Gln Ala Ala Asp
    50                  55                  60

Ser Phe Leu Ser Ser Ile Gly Arg Asp Asn Lys Ile Thr Asn Thr Ala
65                  70                  75                  80

Ser Leu Leu Ala Ser Leu Asp Asn Ile Phe Leu Asn Leu Arg Asn Val
                85                  90                  95

Ser Arg Asp Ile Arg Glu Thr Gly Lys Phe Lys Pro Asn Asp Ile Gln
            100                 105                 110

Gln Ala Ile Gly Asp Ile Phe Ile Ala Ala Gly Asp Gly Leu Gln Tyr
        115                 120                 125

Ile Lys Gln Gln Thr Glu Ala Met Ala Gln Ser Lys Phe Leu Pro Thr
    130                 135                 140

Lys Leu Lys Thr Gly Leu Asn Asp Val Leu Asn Ser Arg Met Leu Lys
145                 150                 155                 160

Ser Ser Thr Val Leu Gln His Glu Leu Asn Tyr Leu Gly Phe Lys Ile
                165                 170                 175

Lys Asp Tyr Gly Asn Glu Arg Leu Gly Glu Ser Ile Met Asn Ile Asp
            180                 185                 190

Asp Phe Thr Pro Ser Lys Ile Ala Asn Phe Phe Ala Asp Pro Asp Thr
        195                 200                 205

Tyr Ser Asn Val Leu Glu Glu Val Ser Arg Phe Ile Tyr Ser Leu Val
    210                 215                 220

Pro Asp Asp Ala Asn Pro Trp Lys Gly Gly Glu Asp Tyr Ile Gly Arg
225                 230                 235                 240

Gly Ile Ser Glu Trp Gly Glu Leu Leu Glu Lys Trp Tyr Lys Gln Asp
                245                 250                 255

Phe Leu Pro Tyr Leu Glu Lys Glu Trp Asp Gln Phe Pro Lys Phe Glu
            260                 265                 270

Asp Trp Leu Pro Glu Phe Pro Glu Trp Ala Arg Glu Trp Leu Lys Leu
```

-continued

```
            275                 280                 285
Asp Pro Lys Arg Ser Gly Lys Tyr His Val Tyr Asp Pro Leu Ala Leu
        290                 295                 300
Asp Leu Asp Gly Asp Gly Ile Glu Thr Val Ala Ala Lys Gly Phe Ala
305                 310                 315                 320
Gly Ala Leu Phe Asp His Arg Asn Gln Gly Ile Arg Thr Ala Thr Gly
                    325                 330                 335
Trp Val Ser Ala Asp Asp Gly Leu Leu Val Arg Asp Leu Asn Gly Asn
                340                 345                 350
Gly Ile Ile Asp Asn Gly Ala Glu Leu Phe Gly Asp Asn Thr Lys Leu
                355                 360                 365
Ala Asp Gly Ser Phe Ala Lys His Gly Tyr Ala Ala Leu Ala Glu Leu
370                 375                 380
Asp Ser Asn Gly Asp Asn Ile Ile Asn Ala Ala Asp Ala Ala Phe Gln
385                 390                 395                 400
Thr Leu Arg Val Trp Gln Asp Leu Asn Gln Asp Gly Ile Ser Gln Ala
                405                 410                 415
Asn Glu Leu Arg Thr Leu Glu Glu Leu Gly Ile Gln Ser Leu Asp Leu
                420                 425                 430
Ala Tyr Lys Asp Val Asn Lys Asn Leu Gly Asn Gly Asn Thr Leu Ala
                435                 440                 445
Gln Gln Gly Ser Tyr Thr Lys Thr Asp Gly Thr Thr Ala Lys Met Gly
                450                 455                 460
Asp Leu Leu Leu Ala Ala Asp Asn Leu His Ser Arg Phe Lys Asp Lys
465                 470                 475                 480
Val Glu Leu Thr Ala Glu Gln Ala Lys Ala Ala Asn Leu Ala Gly Ile
                485                 490                 495
Gly Arg Leu Arg Asp Leu Arg Glu Ala Ala Leu Ser Gly Asp Leu
                500                 505                 510
Ala Asn Met Leu Lys Ala Tyr Ser Ala Ala Glu Thr Lys Glu Ala Gln
                515                 520                 525
Leu Ala Leu Leu Asp Asn Leu Ile His Lys Trp Ala Glu Thr Asp Ser
                535                 540
Asn Trp Gly Lys Lys Ser Pro Met Arg Leu Ser Thr Asp Trp Thr Gln
545                 550                 555                 560
Thr Ala Asn Glu Gly Ile Ala Leu Thr Pro Ser Gln Val Ala Gln Leu
                565                 570                 575
Lys Lys Asn Ala Leu Val Ser Leu Ser Asp Lys Ala Lys Ala Ala Ile
                580                 585                 590
Asp Ala Ala Arg Asp Arg Ile Ala Val Leu Asp Ala Tyr Thr Gly Gln
                595                 600                 605
Asp Ser Ser Thr Leu Tyr Tyr Met Ser Glu Glu Asp Ala Leu Asn Ile
                610                 615                 620
Val Lys Val Thr Asn Asp Thr Tyr Asp His Leu Ala Lys Asn Ile Tyr
625                 630                 635                 640
Gln Asn Leu Leu Phe Gln Thr Arg Leu Gln Pro Tyr Leu Asn Gln Ile
                    645                 650                 655
Ser Phe Lys Met Glu Asn Asp Thr Phe Thr Leu Asp Phe Ser Gly Leu
                660                 665                 670
Val Gln Ala Phe Asn His Val Lys Glu Thr Asn Pro Gln Lys Ala Phe
                675                 680                 685
Val Asp Leu Ala Glu Met Leu Ala Tyr Gly Glu Leu Arg Ser Trp Tyr
                690                 695                 700
```

-continued

```
Glu Gly Arg Arg Leu Met Ala Asp Tyr Val Glu Ala Lys Lys Ala
705                 710                 715                 720

Gly Lys Phe Glu Asp Tyr Gln Lys Val Leu Gly Gln Glu Thr Val Ala
                725                 730                 735

Leu Leu Ala Lys Thr Ser Gly Thr Gln Ala Asp Asp Ile Leu Gln Asn
            740                 745                 750

Val Gly Phe Gly His Asn Lys Asn Val Ser Leu Tyr Gly Asn Asp Gly
        755                 760                 765

Asn Asp Thr Leu Ile Gly Gly Ala Gly Asn Asp Tyr Leu Glu Gly Gly
770                 775                 780

Ser Gly Ser Asp Thr Tyr Val Phe Gly Lys Gly Phe Gly Gln Asp Thr
785                 790                 795                 800

Val Tyr Asn Tyr Asp Tyr Ala Thr Gly Arg Lys Asp Ile Ile Arg Phe
                805                 810                 815

Thr Asp Gly Ile Thr Ala Asp Met Leu Thr Phe Thr Arg Glu Gly Asn
                820                 825                 830

His Leu Leu Ile Lys Ala Lys Asp Asp Ser Gly Gln Val Thr Val Gln
865                 870                 875                 880

Ser Tyr Phe Gln Asn Asp Gly Ser Gly Ala Tyr Arg Ile Asp Glu Ile
850                 855                 860

His Phe Asp Asn Gly Lys Val Leu Asp Val Ala Thr Val Lys Glu Leu
865                 870                 875                 880

Val Gln Gln Ser Thr Asp Gly Ser Asp Arg Leu Tyr Ala Tyr Gln Ser
                885                 890                 895

Gly Ser Thr Leu Asn Gly Gly Leu Gly Asp Asp Tyr Leu Tyr Gly Ala
            900                 905                 910

Asp Gly Asn Asp Leu Leu Asn Gly Asp Ala Gly Asn Asp Ser Ile Tyr
        915                 920                 925

Ser Gly Asn Gly Asn Asp Thr Leu Asp Gly Gly Glu Gly Asn Asp Ala
930                 935                 940

Leu Tyr Gly Tyr Asn Gly Asn Asp Ala Leu Asn Gly Gly Glu Gly Asn
945                 950                 955                 960

Asp His Leu Asn Gly Glu Asp Gly Asn Asp Thr Leu Ile Gly Gly Ala
            965                 970                 975

Gly Asn Asp Tyr Leu Glu Gly Gly Ser Gly Ser Asp Thr Tyr Val Phe
        980                 985                 990

Gly Glu Gly Phe Gly Gln Asp Thr Val Tyr Asn Tyr His Val Asp Lys
    995                 1000                1005

Asn Ser Asp Thr Met His Phe Lys Gly Phe Lys Ala Ala Asp Val His
1010                1015                1020

Phe Ile Arg Ser Gly Ser Asp Leu Val Leu Ser Ala Ser Glu Gln Asp
1025                1030                1035                1040

Asn Val Arg Ile Ser Gly Phe Phe Tyr Gly Glu Asn His Arg Val Asp
                1045                1050                1055

Thr Phe Val Phe Asp Asp Ala Ala Ile Ser Asn Pro Asp Phe Ala Lys
            1060                1065                1070

Tyr Ile Asn Ala Gly Asn Asn Leu Val Gln Ser Met Ser Val Phe Gly
        1075                1080                1085

Ser Asn Thr Ala Ala Thr Gly Gly Asn Val Asp Ala Asn Ile Gln Ser
    1090                1095                1100

Val Gln Gln Pro Leu Leu Val Thr Pro Ser Ala
1105                1110                1115
```